(12) United States Patent
Man

(10) Patent No.: US 7,538,183 B2
(45) Date of Patent: May 26, 2009

(54) HPV VACCINE COMPRISING PEPTIDES FROM HOST CELL PROTEINS

(75) Inventor: Stephen Tze Kwung Man, Heath Park (GB)

(73) Assignee: University College Cardiff Consultants Limited, Cardiff (GB)

( * ) Notice: Subject to any disclaimer, the term of this patent is extended or adjusted under 35 U.S.C. 154(b) by 0 days.

(21) Appl. No.: 11/671,095

(22) Filed: Feb. 5, 2007

(65) Prior Publication Data

US 2007/0218074 A1    Sep. 20, 2007

Related U.S. Application Data

(63) Continuation of application No. PCT/GB2005/002962, filed on Jul. 27, 2005.

(30) Foreign Application Priority Data

Aug. 5, 2004 (GB) ................. 0417430.6

(51) Int. Cl.
*C07K 5/00* (2006.01)
*A61K 39/00* (2006.01)

(52) U.S. Cl. .................... 530/300; 424/184.1

(58) Field of Classification Search .............. None
See application file for complete search history.

(56) References Cited

U.S. PATENT DOCUMENTS

| 6,582,704 | B2 * | 6/2003 | Urban et al. ............. 424/204.1 |
| 7,217,419 | B2 * | 5/2007 | Wettendorff ............. 424/204.1 |
| 7,223,408 | B2 * | 5/2007 | Cassetti et al. ........... 424/204.1 |
| 7,314,629 | B2 * | 1/2008 | Zagury et al. ............ 424/204.1 |
| 2003/0064477 | A1 | 4/2003 | Band et al. |

FOREIGN PATENT DOCUMENTS

DE    198 59 486    12/1998
DE    19859486 A1 *    7/2000
WO    WO 2004/013631    2/2004

OTHER PUBLICATIONS

Hildesheim et al., JAMA, 2007, vol. 298, p. 743-753.*
Hildesheim et al., Journal of Infectious Diseases, 2007, vol. 196, p. 1438-1446.*
Gardasil Merck Product data sheet, p. 1-15.*
Muderspach et al Clinical Cancer Research, 2000, vol. 6, p. 3606-3416.*
Vierboom, et al., High Steady-State Levels of p53 Are Not a Prerequisite for Tumor Eradication by Wild-Type p53-specific Cytotoxic T Lumphocytes, Cancer Research 60, 5508-5513, Oct. 1, 2000.
Scheffner, Martin and Whitaker, Noel J., Human papillomavirus-induced carcinogenesis and the ubiquitin-proteasome system, Seminars in Cancer Biology 13 (2003) 59-67.
Sirianni et al., Effect of Human Papillomavirus-16 Invection on CD8+ T-Cell Recognition of a Wild-type Sequence p53 264-272 Peptide in Patients with Squamous Cell Carcinoma of the Head and Neck, Clinical Cancer Research, vol. 10, 6929-6937, Oct. 15, 2004.

* cited by examiner

*Primary Examiner*—Bruce Campbell
*Assistant Examiner*—Agnieszka Boesen
(74) *Attorney, Agent, or Firm*—King & Schickli, PLLC

(57) ABSTRACT

The present invention relates to a human papillomavirus (HPV) vaccine that comprises peptides from host cell proteins and more particularly, a vaccine that is directed against cancers that are associated with HPV infections, such as cervical cancer, head and neck cancer and skin cancers. The peptides comprise fragments of host cell proteins that have been targeted for degradation by HPV proteins, such as E6 and E7 and are presented on the surface of HPV infected cells in relatively large amounts. These peptides can be recognised by CTL and elicit an immune response, and are therefore ideal tumour-specific markers. The invention also relates to novel peptide: peptide complexes such as peptide/HLA complexes and their use in a tumour-specific vaccine.

6 Claims, 6 Drawing Sheets

HPV VACCINE COMPRISING PEPTIDES FROM HOST CELL PROTEINS

This application is a continuation of international application number PCT/GB2005/002962 (publication no. WO 2006/013336) filed on Jul. 27, 2005 and entitled HPV VACCINE COMPRISING PEPTIDES FROM HOST CELL PROTEINS and claims the benefit of the above-mentioned international application and the corresponding British national patent application no. GB 0417430.6 filed on Aug. 5, 2004 and entitled A NOVEL HPV VACCINE COMPRISING PEPTIDES FROM HOST CELL PROTEINS, the disclosures of each of which are incorporated herein in their entirety by reference.

FIELD OF THE INVENTION

The present invention relates to a human papillomavirus (HPV) vaccine that comprises peptides from host cell proteins and more particularly, but not exclusively, to a vaccine that is directed against cancers that are associated with HPV infections, such as cervical cancer, head and neck cancer and skin cancers. The peptides comprise fragments of host cell proteins that have been targeted for degradation by HPV proteins, such as E6 and E7. Further, the invention relates to the identification of novel peptides and uses thereof. Additionally, the invention relates to novel peptide: peptide complexes and uses thereof.

BACKGROUND TO THE INVENTION

Human papillomavirus (HPV) is a very common virus that causes abnormal growth of tissue on the feet, hands, vocal cords, mouth and genital organs. Over 60 types of HPV have been identified and each type infects certain parts of the body. HPV is mainly spread through physical contact with an infected individual. In the majority of cases, HPV disappears within 1-2 years and indeed, during the course of the infection, may be subclinical; the individual may be unaware of their infection. However, in a small number of cases, HPV can progress and develop into cancer.

There are two kinds of abnormal tissue caused by HPV: condyloma (warts) and dysplasia (pre-cancer). Wart-like growths can be found in any infected areas and may cause itching, burning or slight bleeding. In these instances, antiviral creams may be prescribed or, in some cases, the growth may be removed or destroyed by cold cautery (freezing that destroys tissue) or hot cautery (burning warts off with an electric instrument or laser treatment).

Where HPV infection progresses to cancer, cancer patients are treated by a combination of surgery, radiotherapy and chemotherapy. However, radiotherapy and chemotherapy have the disadvantage of destroying healthy as well as malignant cells, and can thus cause severe side effects, while surgery is invasive and leaves the patient open to secondary infections. These side effects and risks are undesirable, and coupled to this is the fact that these treatments are not always successful, resulting in the majority of patients entering relapse and so representing with the disease.

It is therefore clear that more effective treatments are required, and it has been suggested that the specificity of the immune system might be harnessed against virally infected cells. This concept has been termed "immunotherapy".

In particular, it has been shown that cancer patients have T cells that are capable of recognising their tumour cells, but these cells do not divide and differentiate into cytotoxic T lymphocytes (CTL) which are capable of killing these cells.

Cytotoxic T lymphocytes kill "target" cells, such as virally-infected cells, and have also been implicated in the "immune surveillance" of cancer cells. The majority of CTL belong to the CD8$^+$-subset of T cells and have T-cell receptors (TCR). These TCR are able to recognise peptides when they are expressed on the surface of cells in association with class 1 major histocompatibility complex (MHC) molecules. In man, each class of MHC is represented by more than one locus; these are called human leucocyte antigen (HLA). The class 1 HLA loci are HLA-A, -B, -C, -E, -F and -G. Additionally each HLA has different alleles and Table 1 lists those alleles that have been identified to date.

When a CTL encounters an antigen/MHC complex for which its TCR is specific, it enters the cell cycle and goes through several rounds of mitosis, followed by differentiation into an effector/killer cell. Differentiation includes forming a large number of modified lysosomes that contain the cell-killing proteins perforin and granzyme. Once the CTL have killed the target cells most of them will die, although a small proportion become memory cells that can respond to the antigen quickly if it reappears.

Tumour-reactive cytotoxic T lymphocytes have been shown to mediate tumour regression in animal models (1) and in man (2), and there has thus been an interest in using tumour-specific CTL's as an immunotherapy for human cancers.

In this regard monoclonal antibodies have been shown to be effective against some cancers, especially cancers of white blood cells, and are targeted at a molecule or receptor that is associated with cancer cells. Table 2 lists some of these antibodies and their mechanism of action.

Alternatively, dendritic-cell vaccines have been used to elicit a tumour-specific CTL response. Dendritic cells are the most potent antigen-presenting cells and they act by engulfing antigen, processing it into peptides and presenting it to T cells. To make a dendritic-cell vaccine, dendritic cells are harvested, exposed in vitro to antigen associated with the type of tumour in the patient, and then re-injected into the patient. To date these vaccines have shown some promise against melanoma, prostrate cancer and lymphoma.

Ideally these vaccines target molecules that are expressed on cancer cells, but not on healthy cells. However such tumour-specific antigens have been hard to find, and as a result many of the immune agents now in use also target healthy cells in the hope that these cells, eventually, will be replaced. As with radiotherapy and chemotherapy, this treatment can cause severe side effects and also leads to the potential for autoimmunity (3). Indeed, in the case of a telomerase vaccine, this protein is also present in the stem cells of bone marrow, reproductive organs and perhaps other tissues. Further, the antigen to which some dendritic cells are exposed include tyrosinase, which is to be found in melanocytes, or prostatic acid phosphatase (PAP), which is to be found in prostate cells.

It is therefore clear that additional viral therapies are needed, particularly for those patients with an advanced stage disease that has failed to respond to conventional viral or cancer treatments.

Recently, a number of studies have shown that high-level expression of certain proteins in tumour cells is sufficient to allow CTL to discriminate between tumours and normal cells (4,5).

One way of avoiding autoimmunity in tumour immunotherapy is to target the 15% of human malignancies that are associated with viruses. Of these the strongest association is between cervical cancer and human papillomarivus, with 99.7% of cervical cancers containing HPV DNA (6). There are over 25 HPVs that infect the genital mucosa and give rise to malignancies such as cervical cancer, head and neck cancers and skin cancers. These "high risk" HPVs are characterised by at least two oncogene products: E6 and E7, which act to immortalise and transform, in the cervix, epithelial cells. The expression of these proteins is thought to be essential to retain the transformed phenotype of the cancer cell and so these non-self viral proteins are therefore attractive targets for CTL mediated immunotherapy.

CTL active against HPV E6/E7 can be induced by vaccination (7) and such CTL have been detected with variable frequency in patients with premalignant cervical disease (8) or cancer (9). However it has been difficult to generate these CTL in vitro, probably because they occur at low frequency (10). A major limitation of using these proteins as tumour-specific targets is that they are expressed at low levels in cancer cells (11). Furthermore, the E6 and E7 proteins themselves are small and contain few epitopes suitable for recognition by CTL (12).

The present invention aims to overcome these problems by identifying and then targeting peptides that are recognised by CTL, which peptides are specific to HPV transformed cells and are very unlikely to give rise to autoimmunity. These peptides are either uniquely presented or over-presented in HPV transformed cells, and the proteins from which these peptides are derived are, typically, either absent or appear to be expressed at very low levels in HPV transformed cells. In contrast, these proteins occur at normal or high levels in normal cells.

The invention is based on the mechanism that HPV E6 and E7 oncoproteins use to mediate targeted degradation of host cell proteins such as retinoblastoma proteins (Rb), C-MYC and HMCM7, among others (see Table 3), which takes place during transformation of the infected cell.

It is well known that HPV oncoproteins bind to and facilitate the degradation of host cell proteins, such as Rb. Thus, analysis of HPV transformed cervical carcinomas reveals no apparent expression of full-length Rb protein, whereas normal cells have high cellular levels of the Rb protein, as this is not normally proteolytically degraded (13).

It has been shown that Rb proteins are degraded by the ubiquitin-dependant proteolysis system (13), and more recently, it has come to light that intracellular organelles called proteasomes play a role in mediating degradation (18, 19) of host cell proteins after interaction with E6 or E7 oncoproteins.

We have recognised the fact that the degradation of, for example ubiquinated protein substrates by proteasomes, is possibly the major mechanism by which peptides recognised by CTL's are generated (20, 21). For example, in a virally infected cell, newly synthesised viral proteins in the cytoplasm are degraded by proteasomes into peptide fragments. These peptides are transported into the endoplasmic reticulum (ER) by transporter associated with antigen processing (TAP) proteins. Once inside the ER, the peptides will bind to free MHC class I molecules and beta 2 microglobulin to form a mature MHC/peptide complex. This is transported to the cell surface where it may be recognised by CTL. FIG. 1 shows a diagrammatic representation of this process.

Accordingly, the present invention is based on the theory that in HPV transformed cells, Rb proteins (and other proteins, see Table 3) will be targeted for degradation, processed and peptides thereof will be presented on the surface of the cell as peptides that can be recognised by CTL. In non-HPV transformed, or normal, cells these proteins will not be degraded significantly, so these peptides, effectively, will not be available for CTL recognition. Thus, HPV transformed cells should have high levels of, for example, Rb derived peptides typically co-presented on the cell surface in a peptide HLA complex, but low intracellular levels of the full-length proteins, contrary to normal cells (FIG. 2).

The use of host cell proteins as targets for immunotherapy is not novel. However, in all previous instances this approach has relied on the over-expression of proteins in tumours, compared to normal cells. For example, host cell proteins such as p53 (5), Wilms transcription factor (WT1), Her 2/Neu (16) and hTert (17) have been proposed as "tumour-specific" antigens, as all of these are over-expressed in tumour cells. To our knowledge, this is the first time that a HPV or cancer vaccine has been directed at "tumour-specific" proteins, and more particularly peptides thereof, that are expressed at normal, low, or undetectable levels in HPV transformed cells, compared to normal cells.

Previously, high levels of antigen expression were thought advantageous in order to allow CTL to discriminate between tumour cells and normal cells.

Additionally, up until now HPV vaccines have comprised proteins that are produced by HPV, not host proteins that are targeted for degradation by this virus.

In summary, the current invention relies on a relatively high level of presentation of peptides at the cell surface but not necessarily on relatively high levels of expression, or apparent expression, of the corresponding proteins in the virally-infected cell. In fact, low level or no expression of the tumour-specific protein would typically indicate that the protein was being targeted for degradation by viral proteins and so was present at low intracellular levels, but following degradation, presented at the cell membrane and so was available as a peptide for CTL recognition.

Accordingly, in one aspect of the invention, there is therefore provided a vaccine comprising: at least one isolated, purified, synthesised or recombinant peptide, wherein the peptide is a fragment of a host cell protein that has been degraded by human papillomavirus oncoproteins, and can elicit a CTL response when administered to a mammal.

Reference herein to a cell protein that has been degraded by human papillomavirus oncoproteins includes reference to a protein that has been selectively targeted for degradation by HPV oncoproteins and so includes a protein that, in a HPV transformed cell, would be selectively targeted for degradation or a protein that is acted upon by human HPV oncoproteins in such a way that it is, directly or indirectly, degraded, most typically but not exclusively, by the ubiquitin pathway.

In a preferred embodiment of the invention the mammal is human.

Preferably, the oncoprotein is E6 or E7.

The host cell protein may be any protein that is degraded by viral proteins, such as E6 or E7, and Table 3 lists those proteins that are currently known to be targeted for degradation by E6 or E7.

Preferably, the peptide is HPV-specific or tumour-specific, meaning that it is presented in high amounts on the cell surface of HPV transformed or tumour cells, relative to normal cells.

Even more preferably, the peptide is 9 to 30 amino acids in length.

Alternatively, the peptide may be 9 to 11 amino acids in length.

The CTL response is preferably a HPV-specific or tumour-specific CTL response, meaning that the CTL can recognise HPV transformed cells or tumour cells expressing the peptides of the vaccine.

More preferably, the vaccine comprises one or more of the peptides shown in Table 4 (SEQ ID NOS: 1-161).

More preferably still, the vaccine comprises any of the aforementioned peptides plus a further protein or peptide comprising a major histocompatibility complex molecule, ideally, a class I molecule and more specifically a human leucocyte antigen (HLA), and more ideally still a HLA selected from Table 1.

In another aspect of the invention, there is provided a vaccine comprising: at least one isolated, purified, synthesised or recombinant peptide, wherein the peptide is chosen from those listed in Table 4.

In yet another aspect of the invention, there is provided a vaccine comprising: at least one isolated, purified, synthesised or recombinant peptide selected from Table 4 and, further at least one isolated, purified, synthesised or recombinant HLA selected from those listed in Table 1.

In a further aspect of the invention, there is provided a vaccine comprising: at least one isolated, purified, synthesised or recombinant nucleic acid molecule encoding any peptide or peptide/HLA complex as described above.

In this embodiment, the nucleic acid molecule may be in the form of a vector that comprises a recombinant construct. Ideally the construct is adapted for the expression of said vaccine in a selected host system. The host system is a cell, plasmid, virus, live organism or other similar vehicle.

According to a further aspect of the invention there is provided a host cell transformed or transfected with the vector of the invention.

Additionally, the present invention provides a method of manufacturing a vaccine, which method comprises; culturing a host cell transformed or transfected with a vector comprising a recombinant construct as described above; and isolating/purifying the resulting construct product.

The peptides of the present invention may also be used to generate and isolate HPV-specific or tumour-specific cytotoxic T lymphocytes or their T cell receptors or the genes encoding said receptors, in vitro, for use in adoptive immunotherapy. This could for example be carried out by culturing T lymphocytes with at least one of the peptides described above.

According to yet a further aspect of the invention there is provided a method of identifying HPV-specific or tumour-specific cytotoxic T lymphocytes comprising:
(a) culturing a sample containing cytotoxic T lymphocytes with at least one peptide that represents a fragment of a host cell protein which is degraded by HPV proteins when said host cell is transformed or transfected by HPV whereby said peptide is ultimately presented on a surface of a virally infected cell; and
(b) selecting CTL that recognise said peptide by binding thereto.

In a preferred method of the invention said peptide is one selected from the list shown in Table 4. In yet a further preferred method of the invention the CTL are $CD8^+$ cells.

It will be apparent to those skilled in the art that CTL receptors may further be identified using the aforementioned method.

The present invention can be used to treat HPV associated diseases and particularly cancer, preferably cervical cancer, head and neck squamous cell cancer, non-melanoma skin cancers, liver cancer, mesothioloma or prostrate cancer.

Furthermore, the present invention also provides a method of treatment, which method comprises administering a vaccine as described above, to a mammal to be treated. Ideally, the mammal is human.

According to a further aspect of the invention there is provided a peptide, or a nucleic acid molecule encoding same, selected from the list shown in Table 4.

In a further embodiment of the invention, said peptide is for use as a vaccine and in particular for use as a HPV vaccine to treat HPV associated disorders.

According to a further aspect of the invention there is provided a complex comprising at least one of the peptides listed in Table 4 in association with a HLA co-presenting peptide.

More preferably the HLA peptide is one of the peptides listed in Table 1 and more specifically HLA-A binding protein and more specifically still HLA-A 0201.

According to a further aspect of the invention there is provided the use of a HPV-specific peptide for the production of a HPV vaccine wherein said peptide is a fragment of a mammalian cell protein that has been degraded by human papillomavirus oncoproteins and which is presented, in combination with HLA, at the surface of the transformed or transfected HPV cell whereby the recognition of this peptide HLA complex by a cytotoxic T lymphocyte results in the elicitation of an immune response.

The invention will now be described by way of the following examples and with reference to the following Figures wherein.

Figure 1:
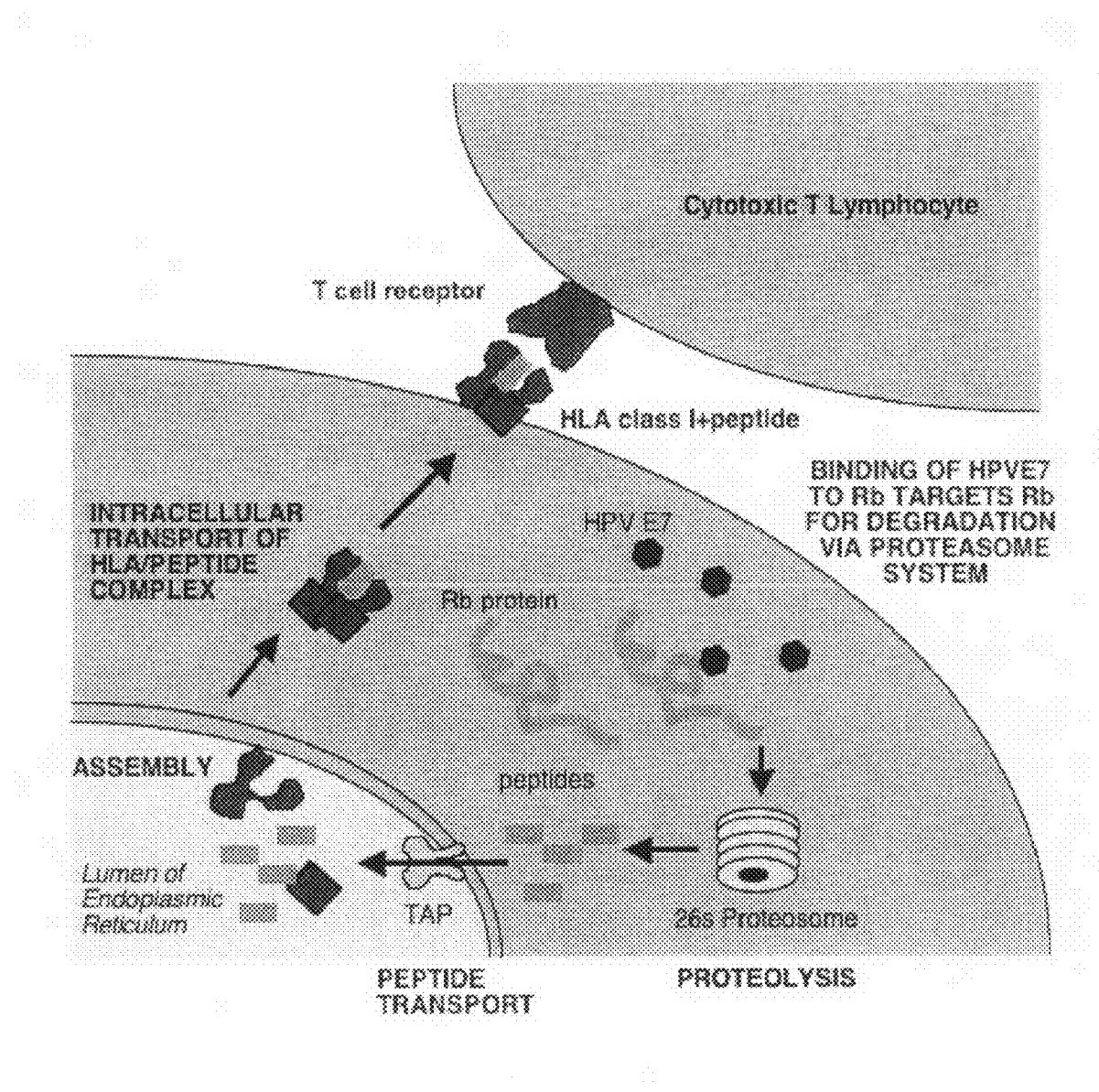
FIG. 1 shows a mechanism for T cell recognition of host cell proteins in cells transformed by human papillomavirus.
Figure 2:
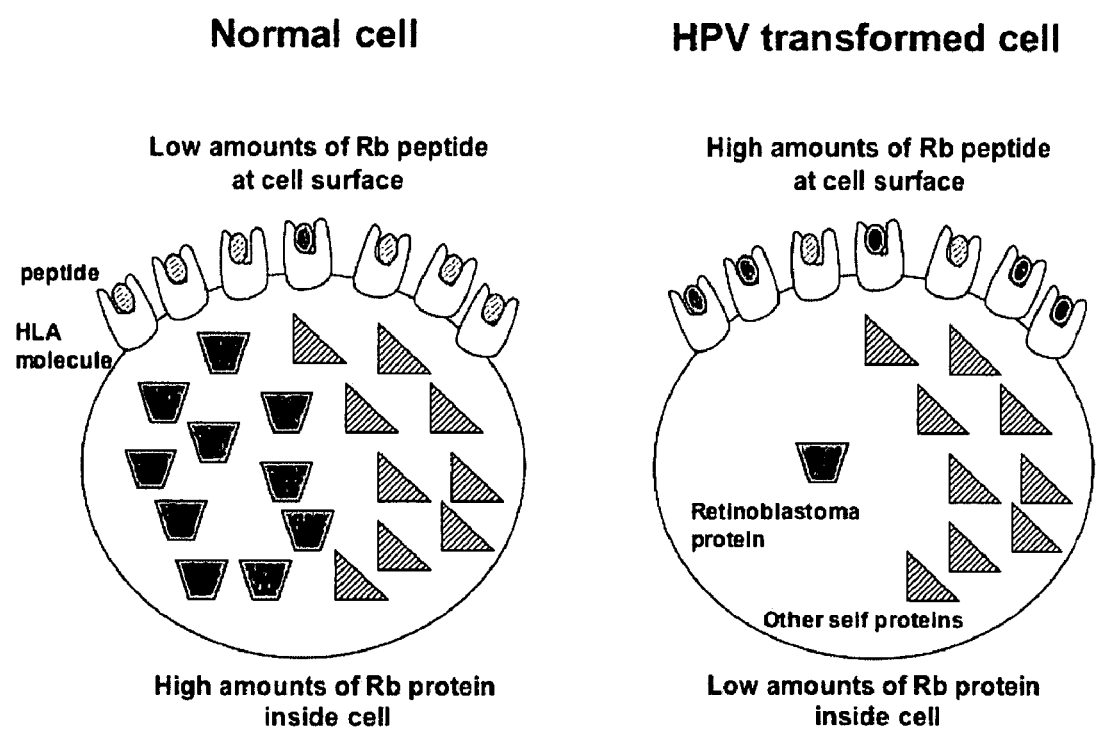
FIG. 2 shows a difference in presentation of host cell peptides in normal and HPV transformed cells.
Figure 3:
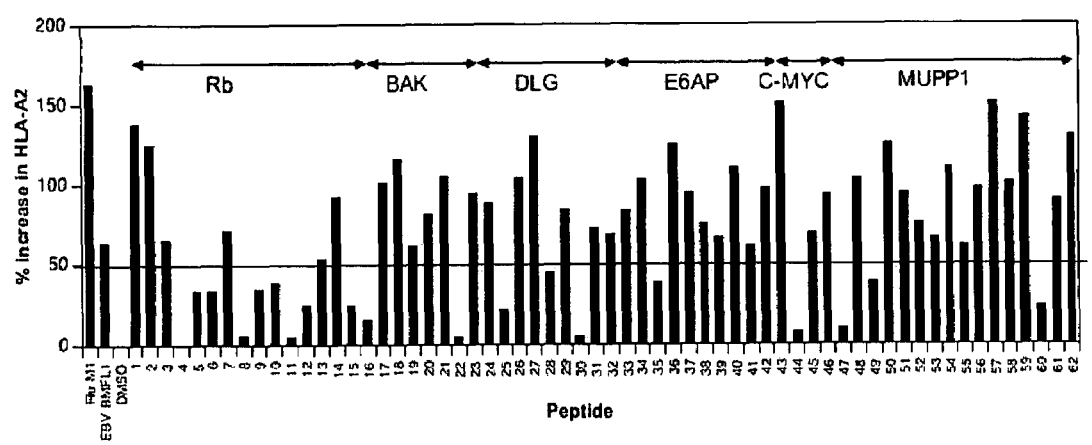
Figure 4:
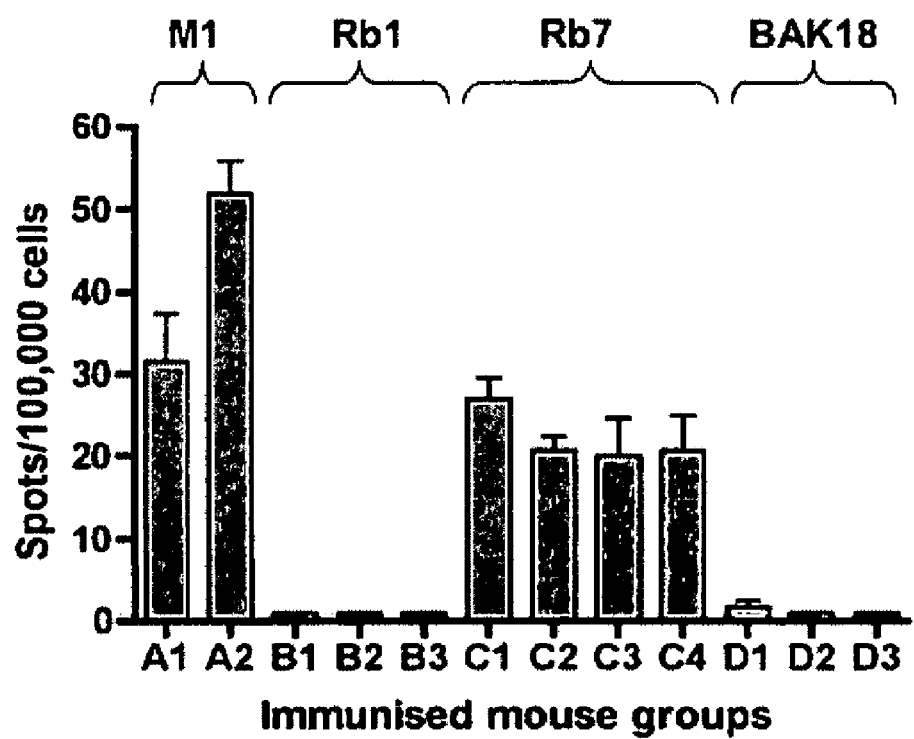
Figure 5:
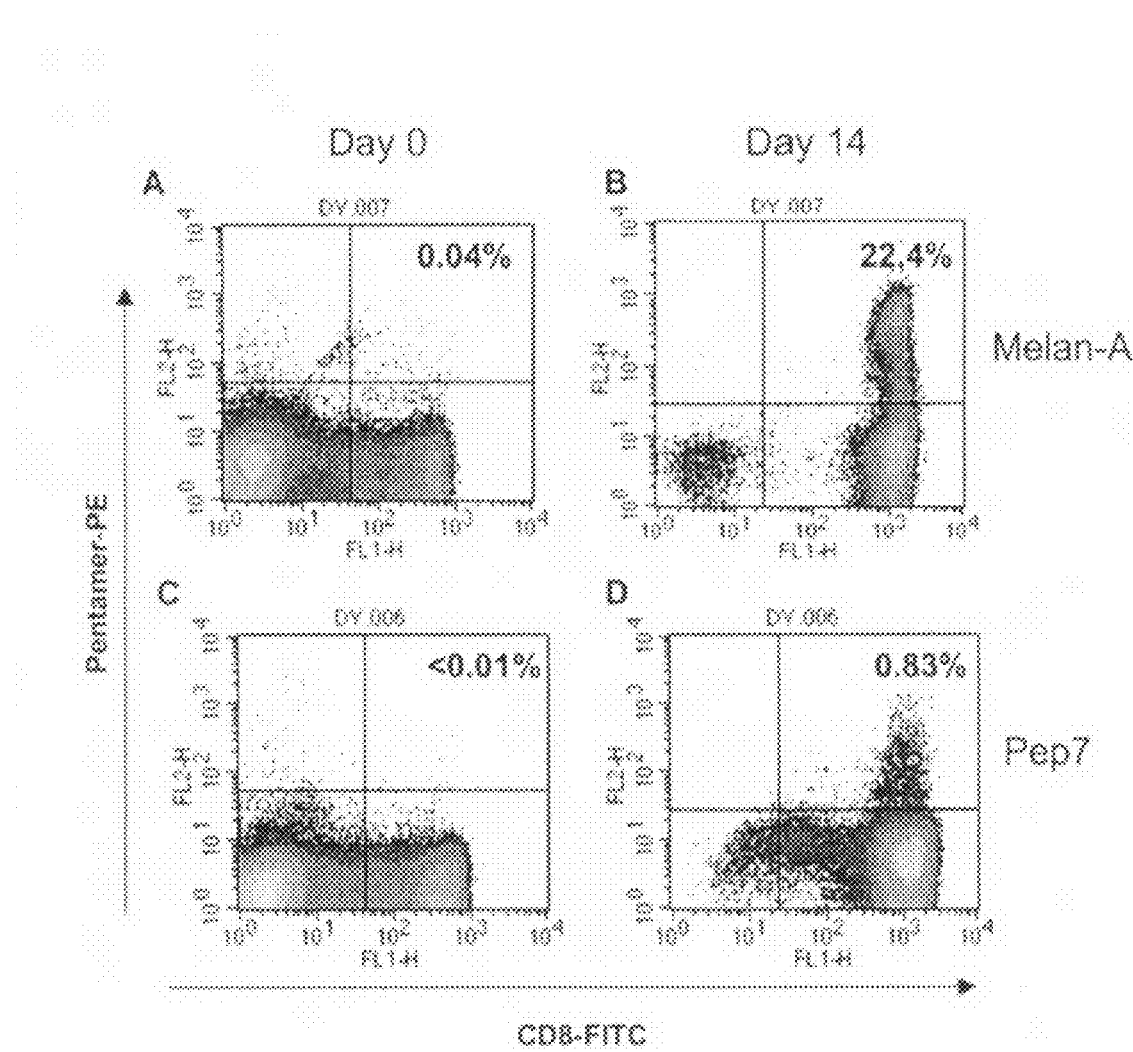
Figure 6:
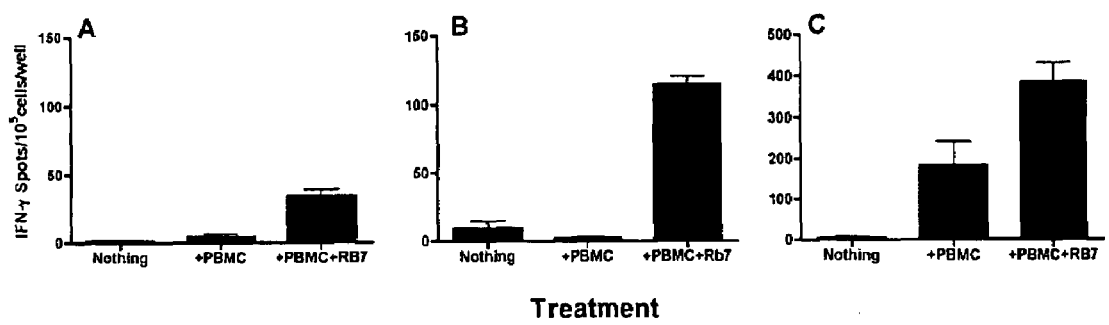

FIG. 3 shows HLA-A2 binding of host protein derived peptides. Specifically, HLA-A*0201 expression of T2 cells was monitored by flow cytometry after overnight incubation with 100 µg test peptides. Each peptide was tested in quadruplicate. A % increase in HLA-A*0201 expression of above 50% was considered significant;

FIG. 4 shows generation of T cell responses in vivo against a peptide derived from human Rb protein. Specifically, HLA-A2/Kb transgenic mice were immunised with 100 µg of test peptide emulsified in incomplete freunds adjuvant. Two to four mice were tested for each peptide. Ten to eleven days later, mice were sacrificed and splenocytes tested in ELISPOT assays. These measured the numbers of IFN☐ producing T cells (spots) specific for the immunising peptide. Positive results were confirmed in at least two further repeat experiments. Representative data from 1 experiment testing $M1_{58-66}$, Rb1, Rb7 and BAK18 peptides, are shown;

FIG. 5 shows $CD8^+$ T cells recognising Rb7 can be detected in healthy $HLA-A2^+$ donors. Specifically, CD8+ T cells were cultured with Rb7 (panels C&D) or Melan-A/Mart1$_{26-35}$ (panels A&B) peptides for 14 days. On day 0 and day 14 days, the numbers of peptide specific $CD8^+$ T cells were measured using appropriate fluoresceinated peptide: HLA-A2 pentamers. These were analysed on a flow cytometer and expressed as % of gated cells, excluding dead and $CD14^+$ cells. Results for donor 5 (from table 4) are shown; and FIG. 6 shows functional $CD8^+$ T cells recognising Rb7 can be detected in healthy donors. Specifically, peripheral blood lymphocytes from $HLA-A2^+$ healthy donors were enriched for CD8+ T cells, then cultured for 14 days with Rb7 peptide and antigen presenting cells (APC). The cultured cells were harvested and tested in enzyme linked immunospot (ELISPOT) assays to measure the numbers of T cells able to secrete IFN-☐ in response to Rb7 peptide. Three (A, B, C) out of seven donors were capable of making significant responses (number of spots for T cells+Rb7+PBMC>2 standard deviations above T cells+PBMC).

EXAMPLE 1

Candidate 9 or 10 amino acid peptides from 15 proteins were selected for analysis, see Table 4 for the full list of peptides. One hundred and two peptides predicted to bind to HLA-A*0201 were selected according to published algorithms (33,34). (Table 4). The algorithm we used has been used previously to successfully predict other tumour-specific CTL epitopes (17). We chose HLA-A*0201 as the co-presenting peptide as this is the most common HLA allele (~40%) among Caucasians, and there are well-defined in vivo and in vitro model systems to facilitate proof of concept experiments. From the initial list of 102 peptides, 62 were synthesized for testing.

Peptides were Tested for Binding to HLA-A*0201.

CTL recognise peptides bound to HLA class I molecules on the cell surface. Therefore peptides must demonstrate binding to HLA to be useful. This can be measured by using a cell based assay measuring an increase in HLA-A*0201 expression resulting from binding.

A cell-based peptide binding assay ((35)) was used to show that the majority (43/62) of candidate peptides could bind to HLA-A*0201 (Table 3, FIG. 3).

HLA-A2 Binding of Host Protein Derived Peptides.

HLA-A*0201 expression of T2 cells was monitored by flow cytometry after overnight incubation with 100 µg test peptides. Each peptide was tested in quadruplicate. A percentage increase in HLA-A*0201 expression of above 50% was considered significant.

The level of binding observed could be classified as either strong or moderate, and was comparable to two well-known HLA-A*0201 restricted CTL epitopes (influenza M1 and EBV BMFL1)(FIG. 3).

43 of the peptides that showed a greater than 50% increase in HLA-A*0201 expression were chosen as candidates for testing in immunogenicity experiments.

Testing In Vivo Immunogenicity in Mice.

We have used HLA-A*0201 transgenic mice to test potential human vaccines (36). These mice can be immunised with peptides together with adjuvant to monitor development of in vivo responses. These responses were detected using ELISPOT assays to measure the numbers of IFN-γ securing peptide specific T cells in the spleen.

This was done with 20 peptides from the Rb(6), Mupp1 (7), BAK (3), DLG (2), AP (2) proteins. All peptides were chosen on the strength of peptide binding (FIG. 3). The $M1_{58-66}$ peptide from influenza, a known HLA-A*0201 binder was used as a positive control. Significant T cell responses were seen against the positive control $M1_{58-66}$ peptide (7/12 mice) and a peptide from $Rb_{485-493}$ (Rb7) protein (7/10 mice). The results are shown in FIG. 4.

Testing In Vitro Immunogenicity using Human T Lymphocytes.

The candidate peptides must be capable of activating human T lymphocytes that can recognise and kill cancer cells. We detected peptide specific T cells in the peripheral blood of patients with cervical cancer. This proved the concept that such peptides can be immunogenic despite being derived from "self" proteins.

Detection of Peptide Specific T Cells

T cells reactive against peptides of the invention should be preferentially found in HLA-A2$^+$ patients with cervical cancer. Blood samples from 4 patients (3 with cervical cancer, 1 with premalignant disease, CIN3) were tested for the presence of CD8$^+$ T cells recognising Rb7 peptide. Fluoresceinated multimeric HLA-A2/peptide complexes were used to measure numbers of peptide specific T cells by flow cytometry (10). This assay demonstrated that T cells specific for Rb7 peptide could be detected at low frequency in the blood of 2 patients with cervical cancer. These frequencies were similar to those previously obtained for HPV16 E7 peptide specific T cells (10). This suggests that it should be possible to isolate and propagate Rb specific T cells for further experiments.

Using the technique described above, T lymphocytes recognising certain "self" tumour antigens such as melan-A can also be readily detected in healthy donors (50). However it is usually the case that T lymphocytes recognising "self" antigens are difficult to detect in healthy donors. Blood samples from 8 healthy donors (all HLA-A2+) were tested for the presence of CD8$^+$ T cells recognising Rb7 peptide and melan-A peptide, using appropriate fluoresceinated multimers (pentamers). T lymphocytes recognising Rb7 peptide could be detected at variable but generally low frequencies in all 8 healthy donors (Table 6). By contrast T lymphocyte responses against melan-A were extremely high frequency, confirming previous reports (50). The highest frequency of T lymphocytes specific for Rb7 was found in donor 5 (FIG. 5).

The assays described above demonstrate that human T cells recognising Rb7 can be detected in both patients and healthy donors. ELISPOT assays were used to determine whether Rb7 peptide specific CD8$^+$ T lymphocytes cultured from healthy donors, were capable of secreting IFN-γ. Seven healthy donors were tested, with 3 donors demonstrating detectable numbers of IFN-γ secreting T lymphocytes (FIG. 5).

Overall these results suggest that host cell protein fragments produced by HPV processing, such as the Rb7 peptide, is immunogenic for human CD8$^+$ T lymphocytes, and can elicit functional (IFN-γ secretion) responses. This suggests that it should be possible to isolate and propagate large numbers of Rb specific T cells for either experimental or clinical therapeutic use.

TABLE 1

Full List of HLA Class I alleles assigned as of July 2005

| HLA-A | HLA-B | HLA-C | HLA-E | HLA-F | HLA-G |
|---|---|---|---|---|---|
| A*01010101 | B*070201 | Cw*010201 | E*01010101 | F*010101 | G*010101 |
| A*01010102N | B*070202 | Cw*010202 | E*01010102 | F*010102 | G*010102 |
| A*010102 | B*070203 | Cw*010203 | E*01030101 | | G*010103 |
| A*010103 | B*070204 | Cw*0103 | E*01030102 | | G*010104 |
| A*0102 | B*0703 | Cw*0104 | E*010302 | | G*010105 |
| A*0103 | B*0704 | Cw*0105 | E*010303 | | G*010106 |
| A*0104N | B*0705 | Cw*0106 | E*010304 | | G*010107 |

TABLE 1-continued

Full List of HLA Class I alleles assigned as of July 2005

| HLA-A | HLA-B | HLA-C | HLA-E | HLA-F | HLA-G |
|---|---|---|---|---|---|
| A*0106 | B*0706 | Cw*0107 | E*0104 | | G*010108 |
| A*0107 | B*0707 | Cw*0108 | | | G*0102 |
| A*0108 | B*0708 | Cw*0109 | | | G*0103 |
| A*0109 | B*0709 | Cw*0110 | | | G*010401 |
| A*0110 | B*0710 | Cw*0111 | | | G*010402 |
| A*0111N | B*0711 | Cw*020201 | | | G*010403 |
| A*0112 | B*0712 | Cw*020202 | | | G*0105N |
| A*0113 | B*0713 | Cw*020203 | | | G*0106 |
| A*0114 | B*0714 | Cw*020204 | | | |
| A*0115N | B*0715 | Cw*020205 | | | |
| A*02010101 | B*0716 | Cw*0203 | | | |
| A*02010102L | B*0717 | Cw*0204 | | | |
| A*020102 | B0718 | Cw*0205 | | | |
| A*020103 | B*0719 | Cw*0206 | | | |
| A*020104 | B*0720 | Cw*0207 | | | |
| A*020105 | B*0721 | Cw*0208 | | | |
| A*020106 | B*0722 | Cw*0209 | | | |
| A*020107 | B*0723 | Cw*0210 | | | |
| A*020108 | B*0724 | Cw*0211 | | | |
| A*020109 | B*0725 | Cw*0212 | | | |
| A*020110 | B*0726 | Cw*030201 | | | |
| A*020111 | B*0727 | Cw*030202 | | | |
| A*0202 | B*0728 | Cw*030301 | | | |
| A*020301 | B*0729 | Cw*030302 | | | |
| A*020302 | B*0730 | Cw*030303 | | | |
| A*0204 | B*0731 | Cw*030304 | | | |
| A*0205 | B*0732 | Cw*030401 | | | |
| A*020601 | B*0733 | Cw*030402 | | | |
| A*020602 | B*0734 | Cw*030403 | | | |
| A*020603 | B*0735 | Cw*0305 | | | |
| A*0207 | B*0736 | Cw*0306 | | | |
| A*0208 | B*0737 | Cw*0307 | | | |
| A*0209 | B*0738 | Cw*0308 | | | |
| A*0210 | B*0739 | Cw*0309 | | | |
| A*0211 | B*0740 | Cw*0310 | | | |
| A*0212 | B*0741 | Cw*0311 | | | |
| A*0213 | B*0742 | Cw*0312 | | | |
| A*0214 | B*0743 | Cw*0313 | | | |
| A*0215N | B*080101 | Cw*0314 | | | |
| A*0216 | B*080102 | Cw*0315 | | | |
| A*021701 | B*0802 | Cw*0316 | | | |
| A*021702 | B*0803 | Cw*0317 | | | |
| A*0218 | B*0804 | Cw*0318 | | | |
| A*0219 | B*0805 | Cw*0319 | | | |
| A*022001 | B*0806 | Cw*04010101 | | | |
| A*022002 | B*0807 | Cw*04010102 | | | |
| A*0221 | B*0808N | Cw*040102 | | | |
| A*0222 | B*0809 | Cw*040103 | | | |
| A*0224 | B*0810 | Cw*0403 | | | |
| A*0225 | B*0811 | Cw*040401 | | | |
| A*0226 | B*0812 | Cw*040402 | | | |
| A*0227 | B*0813 | Cw*0405 | | | |
| A*0228 | B*0814 | Cw*0406 | | | |
| A*0229 | B*0815 | Cw*0407 | | | |
| A*0230 | B*0816 | Cw*0408 | | | |
| A*0231 | B*0817 | Cw*0409N | | | |
| A*0232N | B*0818 | Cw*0410 | | | |
| A*0233 | B*0819N | Cw*0411 | | | |
| A*0234 | B*0820 | Cw*0412 | | | |
| A*023501 | B*0821 | Cw*0413 | | | |
| A*023502 | B*0822 | Cw*0414 | | | |
| A*0236 | B*0823 | Cw*0415 | | | |
| A*0237 | B*0824 | Cw*0416 | | | |
| A*0238 | B*0825 | Cw*0417 | | | |
| A*0239 | B*1301 | Cw*050101 | | | |
| A*0240 | B*130201 | Cw*050102 | | | |
| A*0241 | B*130202 | Cw*0502 | | | |
| A*0242 | B*1303 | Cw*0503 | | | |
| A*0243N | B*1304 | Cw*0504 | | | |
| A*0244 | B*1306 | Cw*0505 | | | |
| A*0245 | B*1307N | Cw*0506 | | | |
| A*0246 | B*1308 | Cw*0507N | | | |
| A*0247 | B*1309 | Cw*0508 | | | |
| A*0248 | B*1310 | Cw*0509 | | | |
| A*0249 | B*1311 | Cw*0510 | | | |

TABLE 1-continued

Full List of HLA Class I alleles assigned as of July 2005

| HLA-A | HLA-B | HLA-C | HLA-E | HLA-F | HLA-G |
|---|---|---|---|---|---|
| A*0250 | B*1312 | Cw*0511 | | | |
| A*0251 | B*1313 | Cw*0602 | | | |
| A*0252 | B*1401 | Cw*0603 | | | |
| A*0253N | B*140201 | Cw*0604 | | | |
| A*0254 | B*140202 | Cw*0605 | | | |
| A*0255 | B*1403 | Cw*0606 | | | |
| A*0256 | B*1404 | Cw*0607 | | | |
| A*0257 | B*1405 | Cw*0608 | | | |
| A*0258 | B*140601 | Cw*0609 | | | |
| A*0259 | B*140602 | Cw*0610 | | | |
| A*0260 | B*1407N | Cw*0611 | | | |
| A*0261 | B*15010101 | Cw*0612 | | | |
| A*0262 | B*15010102N | Cw*0613 | | | |
| A*0263 | B*150102 | Cw*070101 | | | |
| A*0264 | B*150103 | Cw*070102 | | | |
| A*0265 | B*150104 | Cw*070103 | | | |
| A*0266 | B*150105 | Cw*07020101 | | | |
| A*0267 | B*1502 | Cw*07020102 | | | |
| A*0268 | B*1503 | Cw*07020103 | | | |
| A*0269 | B*1504 | Cw*0703 | | | |
| A*0270 | B*1505 | Cw*070401 | | | |
| A*0271 | B*1506 | Cw*070402 | | | |
| A*0272 | B*1507 | Cw*0705 | | | |
| A*0273 | B*1508 | Cw*0706 | | | |
| A*027401 | B*1509 | Cw*0707 | | | |
| A*027402 | B*1510 | Cw*0708 | | | |
| A*0275 | B*151101 | Cw*0709 | | | |
| A*0276 | B*151102 | Cw*0710 | | | |
| A*0277 | B*1512 | Cw*0711 | | | |
| A*0278 | B*1513 | cw*0712 | | | |
| A*0279 | B*1514 | Cw*0713 | | | |
| A*0280 | B*1515 | Cw*0714 | | | |
| A*0281 | B*1516 | Cw*0715 | | | |
| A*0282N | B*15170101 | Cw*0716 | | | |
| A*0283N | B*15170102 | Cw*0717 | | | |
| A*0284 | B*151702 | Cw*0718 | | | |
| A*0285 | B*1518 | Cw*0719 | | | |
| A*0286 | B*1519 | Cw*0720 | | | |
| A*03010101 | B*1520 | Cw*0721 | | | |
| A*03010102N | B*1521 | Cw*0722 | | | |
| A*03010103 | B*1523 | Cw*0723 | | | |
| A*030102 | B*1524 | Cw*0724 | | | |
| A*030103 | B*1525 | Cw*0725 | | | |
| A*030104 | B*1526N | Cw*0726 | | | |
| A*0302 | B*1527 | Cw*0727 | | | |
| A*0303N | B*1528 | Cw*0728 | | | |
| A*0304 | B*1529 | Cw*0729 | | | |
| A*0305 | B*1530 | Cw*0730 | | | |
| A*0306 | B*1531 | Cw*080101 | | | |
| A*0307 | B*1532 | Cw*080102 | | | |
| A*0308 | B*1533 | Cw*0802 | | | |
| A*0309 | B*1534 | Cw*0803 | | | |
| A*0310 | B*1535 | Cw*0804 | | | |
| A*0311N | B*1536 | Cw*0805 | | | |
| A*0312 | B*1537 | Cw*0806 | | | |
| A*0313 | B*1538 | Cw*0807 | | | |
| A*0314 | B*1539 | Cw*0808 | | | |
| A*0315 | B*1540 | Cw*0809 | | | |
| A*0316 | B*1542 | Cw*0810 | | | |
| A*0317 | B*1543 | Cw*0811 | | | |
| A*110101 | B*1544 | Cw*0812 | | | |
| A*110102 | B*1545 | Cw*120201 | | | |
| A*110103 | B*1546 | Cw*120202 | | | |
| A*110104 | B*1547 | Cw*120203 | | | |
| A*110105 | B*1548 | Cw*120301 | | | |
| A*1102 | B*1549 | Cw*120302 | | | |
| A*1103 | B*1550 | Cw*120303 | | | |
| A*1104 | B*1551 | Cw*120401 | | | |
| A*1105 | B*1552 | Cw*120402 | | | |
| A*1106 | B*1553 | Cw*1205 | | | |
| A*1107 | B*1554 | Cw*1206 | | | |
| A*1108 | B*1555 | Cw*1207 | | | |
| A*1109 | B*1556 | Cw*1208 | | | |
| A*1110 | B*1557 | Cw*1209 | | | |
| A*1111 | B*1558 | Cw*1210 | | | |

TABLE 1-continued

Full List of HLA Class I alleles assigned as of July 2005

| HLA-A | HLA-B | HLA-C | HLA-E | HLA-F | HLA-G |
|---|---|---|---|---|---|
| A*1112 | B*1560 | Cw*1211 | | | |
| A*1113 | B*1561 | Cw*1212 | | | |
| A*1114 | B*1562 | Cw*1213 | | | |
| A*1115 | B*1563 | Cw*1214 | | | |
| A*1116 | B*1564 | Cw*1215 | | | |
| A*1117 | B*1565 | Cw*140201 | | | |
| A*1118 | B*1566 | Cw*140202 | | | |
| A*1119 | B*1567 | Cw*140203 | | | |
| A*1120 | B*1568 | Cw*140204 | | | |
| A*1121N | B*1569 | Cw*1403 | | | |
| A*1122 | B*1570 | Cw*1404 | | | |
| A*1123 | B*1571 | Cw*1405 | | | |
| A*2301 | B*1572 | Cw*1406 | | | |
| A*2302 | B*1573 | Cw*1407N | | | |
| A*2303 | B*1574 | Cw*150201 | | | |
| A*2304 | B*1575 | Cw*150202 | | | |
| A*2305 | B*1576 | Cw*1503 | | | |
| A*2306 | B*1577 | Cw*1504 | | | |
| A*2307N | B*1578 | Cw*150501 | | | |
| A*2308N | B*1579N | Cw*150502 | | | |
| A*2309 | B*1580 | Cw*150503 | | | |
| A*2310 | B*1581 | Cw*150504 | | | |
| A*2311N | B*1582 | Cw*1506 | | | |
| A*2312 | B*1583 | Cw*1507 | | | |
| A*24020101 | B*1584 | Cw*1508 | | | |
| A*24020102L | B*1585 | Cw*1509 | | | |
| A*240202 | B*1586 | Cw*1510 | | | |
| A*240203 | B*1587 | Cw*1511 | | | |
| A*240204 | B*1588 | Cw*1512 | | | |
| A*240205 | B*1589 | Cw*1513 | | | |
| A*240206 | B*1590 | Cw*1514 | | | |
| A*240301 | B*1591 | Cw*160101 | | | |
| A*240302 | B*1592 | Cw*160102 | | | |
| A*2404 | B*1593 | Cw*1602 | | | |
| A*2405 | B*1594N | Cw*160401 | | | |
| A*2406 | B*1595 | Cw*1606 | | | |
| A*2407 | B*1596 | Cw*1607 | | | |
| A*2408 | B*1597 | Cw*1701 | | | |
| A*2409N | B*1598 | Cw*1702 | | | |
| A*2410 | B*1599 | Cw*1703 | | | |
| A*2411N | B*180101 | Cw*1801 | | | |
| A*2413 | B*180102 | Cw*1802 | | | |
| A*2414 | B*1802 | | | | |
| A*2415 | B*1803 | | | | |
| A*2417 | B*1804 | | | | |
| A*2418 | B*1805 | | | | |
| A*2419 | B*1806 | | | | |
| A*2420 | B*1807 | | | | |
| A*2421 | B*1808 | | | | |
| A*2422 | B*1809 | | | | |
| A*2423 | B*1810 | | | | |
| A*2424 | B*1811 | | | | |
| A*2425 | B*1812 | | | | |
| A*2426 | B*1813 | | | | |
| A*2427 | B*1814 | | | | |
| A*2428 | B*1815 | | | | |
| A*2429 | B*1817N | | | | |
| A*2430 | B*1818 | | | | |
| A*2431 | B*1819 | | | | |
| A*2432 | B*1820 | | | | |
| A*2433 | B*2701 | | | | |
| A*2434 | B*2702 | | | | |
| A*2435 | B*2703 | | | | |
| A*2436N | B*270401 | | | | |
| A*2437 | B*270402 | | | | |
| A*2438 | B*270502 | | | | |
| A*2439 | B*270503 | | | | |
| A*2440N | B*270504 | | | | |
| A*2441 | B*270505 | | | | |
| A*2442 | B*270506 | | | | |
| A*2443 | B*270507 | | | | |
| A*2444 | B*270508 | | | | |
| A*2445N | B*270509 | | | | |
| A*2446 | B*2706 | | | | |
| A*2447 | B*2707 | | | | |

TABLE 1-continued

Full List of HLA Class I alleles assigned as of July 2005

| HLA-A | HLA-B | HLA-C | HLA-E | HLA-F | HLA-G |
|---|---|---|---|---|---|
| A*2448N | B*2708 | | | | |
| A*2449 | B*2709 | | | | |
| A*2450 | B*2710 | | | | |
| A*2451 | B*2711 | | | | |
| A*2452 | B*2712 | | | | |
| A*2453 | B*2713 | | | | |
| A*250101 | B*2714 | | | | |
| A*250102 | B*2715 | | | | |
| A*2502 | B*2716 | | | | |
| A*2503 | B*2717 | | | | |
| A*2504 | B*2718 | | | | |
| A*260101 | B*2719 | | | | |
| A*260102 | B*2720 | | | | |
| A*260103 | B*2721 | | | | |
| A*260104 | B*2723 | | | | |
| A*2602 | B*2724 | | | | |
| A*2603 | B*2725 | | | | |
| A*2604 | B*2726 | | | | |
| A*2605 | B*2727 | | | | |
| A*2606 | B*2728 | | | | |
| A*260701 | B*2729 | | | | |
| A*260702 | B*2730 | | | | |
| A*2608 | B*350101 | | | | |
| A*2609 | B*350102 | | | | |
| A*2610 | B*350103 | | | | |
| A*2611N | B*350104 | | | | |
| A*2612 | B*350201 | | | | |
| A*2613 | B*350202 | | | | |
| A*2614 | B*3503 | | | | |
| A*2615 | B*350401 | | | | |
| A*2616 | B*350402 | | | | |
| A*2617 | B*3505 | | | | |
| A*2618 | B*3506 | | | | |
| A*2619 | B*3507 | | | | |
| A*2620 | B*3508 | | | | |
| A*2621 | B*350901 | | | | |
| A*2622 | B*350902 | | | | |
| A*2623 | B*3510 | | | | |
| A*2624 | B*3511 | | | | |
| A*2625N | B*3512 | | | | |
| A*2626 | B*3513 | | | | |
| A*29010101 | B*351401 | | | | |
| A*29010102N | B*351402 | | | | |
| A*290201 | B*3515 | | | | |
| A*290202 | B*3516 | | | | |
| A*290203 | B*3517 | | | | |
| A*2903 | B*3518 | | | | |
| A*2904 | B*3519 | | | | |
| A*2905 | B*3520 | | | | |
| A*2906 | B*3521 | | | | |
| A*2907 | B*3522 | | | | |
| A*2908N | B*3523 | | | | |
| A*2909 | B*3524 | | | | |
| A*2910 | B*3525 | | | | |
| A*2911 | B*3526 | | | | |
| A*2912 | B*3527 | | | | |
| A*2913 | B*3528 | | | | |
| A*2914 | B*3529 | | | | |
| A*300101 | B*3530 | | | | |
| A*300102 | B*3531 | | | | |
| A*300201 | B*3532 | | | | |
| A*300202 | B*3533 | | | | |
| A*300203 | B*3534 | | | | |
| A*3003 | B*3535 | | | | |
| A*3004 | B*3536 | | | | |
| A*3006 | B*3537 | | | | |
| A*3007 | B*3538 | | | | |
| A*3008 | B*3539 | | | | |
| A*3009 | B*3540N | | | | |
| A*3010 | B*3541 | | | | |
| A*3011 | B*3542 | | | | |
| A*3012 | B*3543 | | | | |
| A*3013 | B*3544 | | | | |
| A*3014L | B*3545 | | | | |
| A*3015 | B*3546 | | | | |

TABLE 1-continued

Full List of HLA Class I alleles assigned as of July 2005

| HLA-A | HLA-B | HLA-C | HLA-E | HLA-F | HLA-G |
|---|---|---|---|---|---|
| A*310102 | B*3547 | | | | |
| A*3102 | B*3548 | | | | |
| A*3103 | B*3549 | | | | |
| A*3104 | B*3550 | | | | |
| A*3105 | B*3551 | | | | |
| A*3106 | B*3552 | | | | |
| A*3107 | B*3553N | | | | |
| A*3108 | B*3554 | | | | |
| A*3109 | B*3555 | | | | |
| A*3110 | B*3556 | | | | |
| A*3111 | B*3557 | | | | |
| A*3112 | B*3558 | | | | |
| A*3201 | B*3559 | | | | |
| A*3202 | B*3560 | | | | |
| A*3203 | B*3561 | | | | |
| A*3204 | B*3701 | | | | |
| A*3205 | B*3702 | | | | |
| A*3206 | B*3703N | | | | |
| A*3207 | B*3704 | | | | |
| A*3208 | B*3705 | | | | |
| A*3209 | B*3706 | | | | |
| A*3210 | B*3707 | | | | |
| A*3301 | B*3708 | | | | |
| A*330301 | B*3709 | | | | |
| A*330302 | B*3801 | | | | |
| A*3304 | B*380201 | | | | |
| A*3305 | B*380202 | | | | |
| A*3306 | B*3803 | | | | |
| A*3307 | B*3804 | | | | |
| A*3308 | B*3805 | | | | |
| A*3401 | B*3806 | | | | |
| A*3402 | B*3807 | | | | |
| A*3403 | B*3808 | | | | |
| A*3404 | B*3809 | | | | |
| A*3405 | B*3810 | | | | |
| A*3406 | B*3811 | | | | |
| A*3601 | B*39010101 | | | | |
| A*3602 | B*39010102L | | | | |
| A*3603 | B*390103 | | | | |
| A*3604 | B*390104 | | | | |
| A*4301 | B*390201 | | | | |
| A*6601 | B*390202 | | | | |
| A*6602 | B*3903 | | | | |
| A*6603 | B*3904 | | | | |
| A*6604 | B*3905 | | | | |
| A*680101 | B*390601 | | | | |
| A*680102 | B*390602 | | | | |
| A*680103 | B*3907 | | | | |
| A*6802 | B*3908 | | | | |
| A*680301 | B*3909 | | | | |
| A*680302 | B*3910 | | | | |
| A*6804 | B*3911 | | | | |
| A*6805 | B*3912 | | | | |
| A*6806 | B*391301 | | | | |
| A*6807 | B*391302 | | | | |
| A*6808 | B*3914 | | | | |
| A*6809 | B*3915 | | | | |
| A*6810 | B*3916 | | | | |
| A*6811N | B*3917 | | | | |
| A*6812 | B*3918 | | | | |
| A*6813 | B*3919 | | | | |
| A*6814 | B*3920 | | | | |
| A*6815 | B*3922 | | | | |
| A*6816 | B*3923 | | | | |
| A*6817 | B*3924 | | | | |
| A*6818N | B*3925N | | | | |
| A*6819 | B*3926 | | | | |
| A*6820 | B*3927 | | | | |
| A*6821 | B*3928 | | | | |
| A*6822 | B*3929 | | | | |
| A*6823 | B*3930 | | | | |
| A*6824 | B*3931 | | | | |
| A*6825 | B*3932 | | | | |
| A*6826 | B*3933 | | | | |
| A*6827 | B*3934 | | | | |

TABLE 1-continued

Full List of HLA Class I alleles assigned as of July 2005

| HLA-A | HLA-B | HLA-C | HLA-E | HLA-F | HLA-G |
|-------|-------|-------|-------|-------|-------|
| A*6828 | B*400101 | | | | |
| A*6901 | B*400102 | | | | |
| A*7401 | B*400103 | | | | |
| A*7402 | B*400104 | | | | |
| A*7403 | B*400105 | | | | |
| A*7404 | B*400201 | | | | |
| A*7405 | B*400202 | | | | |
| A*7406 | B*400203 | | | | |
| A*7407 | B*4003 | | | | |
| A*7408 | B*4004 | | | | |
| A*7409 | B*4005 | | | | |
| A*7410 | B*40060101 | | | | |
| A*7411 | B*40060102 | | | | |
| A*8001 | B*400602 | | | | |
| | B*4007 | | | | |
| | B*4008 | | | | |
| | B*4009 | | | | |
| | B*4010 | | | | |
| | B*4011 | | | | |
| | B*4012 | | | | |
| | B*4013 | | | | |
| | B*401401 | | | | |
| | B*401402 | | | | |
| | B*401403 | | | | |
| | B*4015 | | | | |
| | B*4016 | | | | |
| | B*4018 | | | | |
| | B*4019 | | | | |
| | B*4020 | | | | |
| | B*4021 | | | | |
| | B*4022N | | | | |
| | B*4023 | | | | |
| | B*4024 | | | | |
| | B*4025 | | | | |
| | B*4026 | | | | |
| | B*4027 | | | | |
| | B*4028 | | | | |
| | B*4029 | | | | |
| | B*4030 | | | | |
| | B*4031 | | | | |
| | B*4032 | | | | |
| | B*4033 | | | | |
| | B*4034 | | | | |
| | B*4035 | | | | |
| | B*4036 | | | | |
| | B*4037 | | | | |
| | B*4038 | | | | |
| | B*4039 | | | | |
| | B*4040 | | | | |
| | B*4042 | | | | |
| | B*4043 | | | | |
| | B*4044 | | | | |
| | B*4045 | | | | |
| | B*4046 | | | | |
| | B*4047 | | | | |
| | B*4048 | | | | |
| | B*4049 | | | | |
| | B*4050 | | | | |
| | B*4051 | | | | |
| | B*4052 | | | | |
| | B*4053 | | | | |
| | B*4054 | | | | |
| | B*4055 | | | | |
| | B*4056 | | | | |
| | B*4057 | | | | |
| | B*4058 | | | | |
| | B*4059 | | | | |
| | B*4060 | | | | |
| | B*4061 | | | | |
| | B*4101 | | | | |
| | B*4102 | | | | |
| | B*4103 | | | | |
| | B*4104 | | | | |
| | B*4105 | | | | |
| | B*4106 | | | | |

TABLE 1-continued

Full List of HLA Class I alleles assigned as of July 2005

| HLA-A | HLA-B | HLA-C | HLA-E | HLA-F | HLA-G |
|---|---|---|---|---|---|
| | B*4107 | | | | |
| | B*4201 | | | | |
| | B*4202 | | | | |
| | B*4204 | | | | |
| | B*420501 | | | | |
| | B*420502 | | | | |
| | B*4206 | | | | |
| | B*44020101 | | | | |
| | B*44020102S | | | | |
| | B*440202 | | | | |
| | B*440203 | | | | |
| | B*440301 | | | | |
| | B*440302 | | | | |
| | B*4404 | | | | |
| | B*4405 | | | | |
| | B*4406 | | | | |
| | B*4407 | | | | |
| | B*4408 | | | | |
| | B*4409 | | | | |
| | B*4410 | | | | |
| | B*4411 | | | | |
| | B*4412 | | | | |
| | B*4413 | | | | |
| | B*4414 | | | | |
| | B*4415 | | | | |
| | B*4416 | | | | |
| | B*4417 | | | | |
| | B*4418 | | | | |
| | B*4419N | | | | |
| | B*4420 | | | | |
| | B*4421 | | | | |
| | B*4422 | | | | |
| | B*4423N | | | | |
| | B*4424 | | | | |
| | B*4425 | | | | |
| | B*4426 | | | | |
| | B*4427 | | | | |
| | B*4428 | | | | |
| | B*4429 | | | | |
| | B*4430 | | | | |
| | B*4431 | | | | |
| | B*4432 | | | | |
| | B*4433 | | | | |
| | B*4434 | | | | |
| | B*4435 | | | | |
| | B*4436 | | | | |
| | B*4437 | | | | |
| | B*4438 | | | | |
| | B*4439 | | | | |
| | B*4440 | | | | |
| | B*4441 | | | | |
| | B*4442 | | | | |
| | B*4501 | | | | |
| | B*4502 | | | | |
| | B*4503 | | | | |
| | B*4504 | | | | |
| | B*4505 | | | | |
| | B*4506 | | | | |
| | B*4507 | | | | |
| | B*4601 | | | | |
| | B*4602 | | | | |
| | B*4603 | | | | |
| | B*4604 | | | | |
| | B*4605 | | | | |
| | B*47010101 | | | | |
| | B*47010102 | | | | |
| | B*4702 | | | | |
| | B*4703 | | | | |
| | B*4704 | | | | |
| | B*4705 | | | | |
| | B*4801 | | | | |
| | B*4802 | | | | |
| | B*4803 | | | | |
| | B*4804 | | | | |
| | B*4805 | | | | |

TABLE 1-continued

Full List of HLA Class I alleles assigned as of July 2005

| HLA-A | HLA-B | HLA-C | HLA-E | HLA-F | HLA-G |
|---|---|---|---|---|---|
| | B*4806 | | | | |
| | B*4807 | | | | |
| | B*4808 | | | | |
| | B*4809 | | | | |
| | B*4810 | | | | |
| | B*4811 | | | | |
| | B*4812 | | | | |
| | B*4813 | | | | |
| | B*4901 | | | | |
| | B*4902 | | | | |
| | B*4903 | | | | |
| | B*4904 | | | | |
| | B*5001 | | | | |
| | B*5002 | | | | |
| | B*5004 | | | | |
| | B*510101 | | | | |
| | B*510102 | | | | |
| | B*510103 | | | | |
| | B*510104 | | | | |
| | B*510105 | | | | |
| | B*510106 | | | | |
| | B*510107 | | | | |
| | B*510201 | | | | |
| | B*510202 | | | | |
| | B*5103 | | | | |
| | B*5104 | | | | |
| | B*5105 | | | | |
| | B*5106 | | | | |
| | B*5107 | | | | |
| | B*5108 | | | | |
| | B*5109 | | | | |
| | B*5110 | | | | |
| | B*5111N | | | | |
| | B*5112 | | | | |
| | B*511301 | | | | |
| | B*511302 | | | | |
| | B*5114 | | | | |
| | B*5115 | | | | |
| | B*5116 | | | | |
| | B*5117 | | | | |
| | B*5118 | | | | |
| | B*5119 | | | | |
| | B*5120 | | | | |
| | B*5121 | | | | |
| | B*5122 | | | | |
| | B*5123 | | | | |
| | B*5124 | | | | |
| | B*5126 | | | | |
| | B*5127N | | | | |
| | B*5128 | | | | |
| | B*5129 | | | | |
| | B*5130 | | | | |
| | B*5131 | | | | |
| | B*5132 | | | | |
| | B*5133 | | | | |
| | B*5134 | | | | |
| | B*5135 | | | | |
| | B*5136 | | | | |
| | B*5137 | | | | |
| | B*5138 | | | | |
| | B*520101 | | | | |
| | B*520102 | | | | |
| | B*520103 | | | | |
| | B*520104 | | | | |
| | B*5202 | | | | |
| | B*5203 | | | | |
| | B*5204 | | | | |
| | B*5205 | | | | |
| | B*5206 | | | | |
| | B*5207 | | | | |
| | B*5208 | | | | |
| | B*530101 | | | | |
| | B*530102 | | | | |
| | B*530103 | | | | |
| | B*5302 | | | | |

TABLE 1-continued

Full List of HLA Class I alleles assigned as of July 2005

| HLA-A | HLA-B | HLA-C | HLA-E | HLA-F | HLA-G |
|---|---|---|---|---|---|
| | B*5303 | | | | |
| | B*5304 | | | | |
| | B*5305 | | | | |
| | B*5306 | | | | |
| | B*5307 | | | | |
| | B*5308 | | | | |
| | B*5309 | | | | |
| | B*5310 | | | | |
| | B*5401 | | | | |
| | B*5402 | | | | |
| | B*5403 | | | | |
| | B*5404 | | | | |
| | B*5405N | | | | |
| | B*5406 | | | | |
| | B*5407 | | | | |
| | B*550101 | | | | |
| | B*550102 | | | | |
| | B*5502 | | | | |
| | B*5503 | | | | |
| | B*5504 | | | | |
| | B*5505 | | | | |
| | B*5507 | | | | |
| | B*5508 | | | | |
| | B*5509 | | | | |
| | B*5510 | | | | |
| | B*5511 | | | | |
| | B*5512 | | | | |
| | B*5513 | | | | |
| | B*5514 | | | | |
| | B*5515 | | | | |
| | B*5516 | | | | |
| | B*5517 | | | | |
| | B*5518 | | | | |
| | B*5519 | | | | |
| | B*5601 | | | | |
| | B*5602 | | | | |
| | B*5603 | | | | |
| | B*5604 | | | | |
| | B*560501 | | | | |
| | B*560502 | | | | |
| | B*5606 | | | | |
| | B*5607 | | | | |
| | B*5608 | | | | |
| | B*5609 | | | | |
| | B*5610 | | | | |
| | B*5611 | | | | |
| | B*5612 | | | | |
| | B*5613 | | | | |
| | B*5614 | | | | |
| | B*5615 | | | | |
| | B*5616 | | | | |
| | B*570101 | | | | |
| | B*570102 | | | | |
| | B*570103 | | | | |
| | B*5702 | | | | |
| | B*570301 | | | | |
| | B*570302 | | | | |
| | B*5704 | | | | |
| | B*5705 | | | | |
| | B*5706 | | | | |
| | B*5707 | | | | |
| | B*5708 | | | | |
| | B*5709 | | | | |
| | B*5801 | | | | |
| | B*5802 | | | | |
| | B*5804 | | | | |
| | B*5805 | | | | |
| | B*5806 | | | | |
| | B*5807 | | | | |
| | B*5808 | | | | |
| | B*5809 | | | | |
| | B*5810N | | | | |
| | B*5811 | | | | |
| | B*5901 | | | | |
| | B*670101 | | | | |

TABLE 1-continued

Full List of HLA Class I alleles assigned as of July 2005

| HLA-A | HLA-B | HLA-C | HLA-E | HLA-F | HLA-G |
|---|---|---|---|---|---|
| | B*670102 | | | | |
| | B*6702 | | | | |
| | B*7301 | | | | |
| | B*7801 | | | | |
| | B*780201 | | | | |
| | B*780202 | | | | |
| | B*7803 | | | | |
| | B*7804 | | | | |
| | B*7805 | | | | |
| | B*8101 | | | | |
| | B*8102 | | | | |
| | B*8201 | | | | |
| | B*8202 | | | | |
| | B*8301 | | | | |
| | B*9501 | | | | |
| | B*9502 | | | | |
| | B*9503 | | | | |
| | B*9504 | | | | |

TABLE 2

Monoclonal antibodies used to treat cancer, their target and mechanism of action.

| Name of monoclonal antibody | Target/Mechanism of action |
|---|---|
| Rituximab (Rituxan ®) | Used to treat B-cell lymphomas, acts by binding to the CD20 molecule present on all B cells. |
| Herceptin ® | Binds to HER2, a growth factor receptor found on some tumour cells, such as breast cancers and lymphomas. |
| Alemtuzumab (MabCampath ®) | Used to treat chronic lymphocytic leukaemia. Binds to the CD52 molecule found on all white blood cells. |
| Lym-1 (Oncolym ®) | Used to treat lymphoma. Binds to the histocompatibility antigen found on lymphoma cells. |
| Bevacizumab (Avastin ®) | Used to treat tumours. Binds to vascular endothelial growth factor, which is found in healthy as well as malignant cells. |
| Cetuximab (Erbitux ®) | Used to treat colorectal cancers. Binds to epidermal growth factor receptor, which is also found on normal epithelial cells. |
| Telomerase antibody | Used to treat cancers in general. Binds to telomerase, which is the protein responsible for cancer cells over-riding the usual apoptosis mechanisms. This protein is also present on normal cells. |

TABLE 3

Host cell proteins known to be targeted for degradation following binding to HPV E6 or E7 proteins.

| Host cell target* | HPV protein | Other names | Gene name | Accession number | Function | Location | Reference |
|---|---|---|---|---|---|---|---|
| Retinoblastoma 1 | E7 | Retinoblastoma susceptibility protein | RB1 | M15400 | cell cycle regulation, tumour suppressor | Nuclear | (19) |
| E6AP | E6 | Human papillomavirus E6 associated protein (E6AP), Ubiquitin protein ligase E3A (UBE3A) | UBE3A | AF002224 | proteolysis; binds to HPV16&18 E6 to target p53 for degradation, can also target itself for ubiquination and degradation | Cytosolic | (24) |
| C-MYC | E6 | v-myc myelocytomatosis viral oncogene | MYC | AY214166 | cell cycle, gene transcription | Nuclear | (25) |

TABLE 3-continued

Host cell proteins known to be targeted for degradation following binding to HPV E6 or E7 proteins.

| Host cell target* | HPV protein | Other names | Gene name | Accession number | Function | Location | Reference |
|---|---|---|---|---|---|---|---|
| | | homolog (avian), myc protooncogene product | | | | | |
| HSCRIB | E6 | scribbled homologue, vartul | SCRIB | AY062238 | cell cycle | membrane | (26) |
| HMCM7 | E6 | minichromosome maintenance deficient 7, CDC47 | MCM7 | AB004270 | DNA replication | nuclear | (27) |
| MAGI1 | E6 | membrane associated guanylate kinase, WW and PDZ domain containing 1, BAIAP1, BAP1, MAGI-1, AIP3 | MAGI1 | AB010894 | Signalling, tight junctions, cell adhesion | membrane | (28) |
| SIPA1L1 | E6 | signal-induced proliferation-associated 1 like 1, E6 targetted protein 1 (E6TP1) | SIPA1L1 | AB007900 | GTPase activating protein | membrane | (29) |
| DLG1 | E6 | discs, large homolog 1 (DLG1, HDLG), synapse associated protein 97 (SAP97), hdlg | DLG1 | U13897 | cell growth, adhesion, signalling | membrane | (30) |
| BAK | E6 | BCL2-antagonist/killer 1 | BAK1 | U23765 | proapoptotic, in presence of appropriate stimuli binds to BCL-2 to accelerate cell death | membrane | (31) |
| MPDZ | E6 | multiple PDZ domain protein (MUPP1) | MPDZ | AF093419 | tight junction formation | membrane | (32) |
| MGMT | E6 | 0-6-methylguanine-DNA methyltransferase | MGMT | M29971 | DNA repair | nuclear | (33) |
| MAGI-2 | E6 | membrane associated guanylate kinase, WW and PDZ domain containing 2, activin receptor interacting protein 1 (ARIP1) | MAGI2 | AB014605 | same as magi-1 | membrane | (34) |
| MAGI-3 | E6 | membrane associated guanylate kinase, WW and PDZ domain containing 3 | MAGI3 | AF213259 | same as magi-1 | membrane | (34) |
| Tuberin | E6 | tuberous sclerosis 2 (TSC2) | TSC2 | AB014460 | tumour suppressor, GTPase signalling | membrane | (35) |
| N-MYC | E6 | v-myc myelocytomatosis viral related oncogene, neuroblastoma derived (avian), N-MYC proto-oncogene protein | MYCN | M13228 | tumour suppressor | membrane | (25) |

*Proteins are listed by their agreed standard names, rather than the published names.

TABLE 4

Host cell proteins and HLA-A*0201 binding peptides

| Protein | Starting Pos | Sequence | T0.5 | SEQ ID NO. |
|---|---|---|---|---|
| Retinoblastoma | 563 | WLSDsPLFDL | 5375 | 1 |
| Retinoblastoma | 475 | KLLNdNIFHM | 858 | 2 |
| Retinoblastoma | 75 | WLTWeKVSSV | 736 | 3 |
| Retinoblastoma | 646 | SLSLFYKKV | 396 | 4 |
| Retinoblastoma | 447 | KLGVrLYYRV | 365 | 5 |
| Retinoblastoma | 218 | LMLCvLDYFI | 261 | 6 |
| Retinoblastoma | 485 | SLLACALEV | 257 | 7 |
| Retinoblastoma | 157 | VLFALFSKL | 255 | 8 |
| Retinoblastoma | 648 | SLFYkKVYRL | 182 | 9 |
| Retinoblastoma | 824 | KMTPrSRILV | 176 | 10 |
| Retinoblastoma | 679 | IIWTIFQHTL | 157 | 11 |
| Retinoblastoma | 188 | ALVLKVSWI | 132 | 12 |
| Retinoblastoma | 76 | LTWEKVSSV | 129 | 13 |
| Retinoblastoma | 703 | IMMCSMYGI | 109 | 14 |
| Retinoblastoma | 900 | KLAEmTSTRT | 107 | 15 |
| Retinoblastoma | 219 | MLCVLDYFI | 98 | 16 |
| BAK | 150 | FLGQvTRFVV | 761 | 17 |
| BAK | 129 | ALLGFGYRL | 300 | 18 |
| BAK | 188 | ILNVIVVLGV | 272 | 19 |
| BAK | 182 | NLGNgPILNV | 160 | 20 |
| BAK | 195 | VVLLGQFVV | 91 | 21 |
| BAK | 191 | VLVVIGVVLL | 84 | 22 |
| BAK | 145 | GLTGFLGQV | 79 | 23 |
| DLG | 355 | ALYDRLADV | 2099 | 24 |
| DLG | 275 | NLHGvFVAEV | 608 | 25 |
| DLG | 345 | GLPGDSFYI | 333 | 26 |
| DLG | 148 | QLLEfNGINL | 324 | 27 |
| DLG | 666 | VLWIPACPL | 301 | 28 |
| DLG | 497 | VLILgPLLDV | 272 | 29 |
| DLG | 301 | LILEyGSLDV | 247 | 30 |
| DLG | 480 | SLAYqRVQKV | 160 | 31 |
| DLG | 498 | LILGPLLDV | 138 | 32 |
| DLG | 178 | ILAQYNPHV | 118 | 33 |
| E6AP | 127 | YLTEeKVYEI | 453 | 34 |
| E6AP | 449 | FINEPLNEV | 415 | 35 |
| E6AP | 748 | YLFRpEEIEL | 364 | 36 |
| E6AP | 657 | VLYQSLKDL | 267 | 37 |
| E6AP | 785 | VLIREFWEI | 253 | 38 |
| E6AP | 226 | KLGPDDVSV | 243 | 39 |
| E6AP | 283 | YLNLFIIGM | 200 | 40 |
| E6AP | 785 | VLIReFWEIV | 153 | 41 |
| E6AP | 477 | FMTCpFILNA | 144 | 42 |
| E6AP | 262 | YLSPnVECDL | 98 | 43 |
| C-MYC | 133 | CMWSgFSAAA | 113 | 44 |
| C-MYC | 68 | GLCSpSYVAV | 104 | 45 |
| C-MYC | 177 | YLQDLSAAA | 94 | 46 |
| C-MYC | 133 | CMWSGFSAA | 57 | 47 |
| MUPP1 | 745 | LLPGdRLMFV | 1496 | 48 |
| MUPP1 | 692 | AMWEaGIQHI | 590 | 49 |
| MUPP1 | 607 | LLGENHQDV | 485 | 50 |
| MUPP1 | 981 | YLLEQSSLA | 347 | 51 |
| MUPP1 | 1650 | LLGAiIIHEV | 272 | 52 |
| MUPP1 | 814 | GLADkPLFRA | 272 | 53 |
| MUPP1 | 606 | TLLGeNHQDV | 257 | 54 |
| MUPP1 | 1547 | SLLKtAKMTV | 257 | 55 |
| MUPP1 | 1772 | ILMVNGEDV | 214 | 56 |
| MUPP1 | 1524 | KVGDQILAV | 201 | 57 |
| MUPP1 | 1766 | LMQGdQILMV | 196 | 58 |
| MUPP1 | 592 | KLFSGDELL | 136 | 59 |
| MUPP1 | 87 | TLQNESFLL | 124 | 60 |
| MUPP1 | 312 | GMSSeQVAQV | 116 | 61 |
| MUPP1 | 751 | LMFVNDVNL | 97 | 62 |
| E6TP1 | 855 | SMGAIVWAV | 867 | 63 |
| E6TP1 | 886 | VLIEqETKSV | 485 | 64 |
| E6TP1 | 960 | GLGQLGFHV | 403 | 65 |
| E6TP1 | 877 | LLGIsNEFIV | 281 | 66 |
| E6TP1 | 1009 | QMIDILRTSV | 206 | 67 |
| E6TP1 | 1592 | VLFSsTYPSL | 202 | 68 |
| E6TP1 | 783 | FLLAKVINA | 194 | 69 |
| E6TP1 | 45 | SLGSsVMAPV | 160 | 70 |
| E6TP1 | 641 | FLQLLGERV | 157 | 71 |
| E6TP1 | 339 | ILFDLNEAI | 132 | 72 |
| E6TP1 | 1522 | KLIDLESPT | 107 | 73 |
| MAGI-1 | 69 | LLLEvQGVRV | 1794 | 74 |
| MAGI-1 | 262 | TLQEtALPPV | 656 | 75 |
| MAGI-1 | 1054 | KVGDRILAV | 201 | 76 |
| MAGI-1 | 161 | FLTVkEFLDL | 187 | 77 |
| MAGI-1 | 80 | GLPRyDVLGV | 160 | 78 |
| MAGI-1 | 717 | LLVQrGGLPV | 118 | 79 |
| MAGI-1 | 527 | VLGHTHAQV | 118 | 80 |
| MCM7 | 356 | RLAQHITYV | 880 | 81 |
| MCM7 | 335 | LLSRfDLLWL | 459 | 82 |
| MCM7 | 60 | KMQEHSDQV | 353 | 83 |
| MCM7 | 259 | VLADqGVCCI | 167 | 84 |
| MCM7 | 439 | ALARIRMVDV | 160 | 85 |
| MCM7 | 381 | KLMRrYIAMC | 148 | 86 |
| MCM7 | 178 | LLLLLVGGV | 131 | 87 |
| MCM7 | 481 | ALDEyEELNV | 114 | 88 |
| MCM7 | 273 | KMAEaDRTAI | 108 | 89 |
| Vartul | 713 | KLLEvNGVAL | 1134 | 90 |
| Vartul | 99 | SLPAsLSFLV | 403 | 91 |
| Vartul | 348 | YLLPQQPPL | 364 | 92 |
| Vartul | 229 | ILTEnLLMAL | 342 | 93 |
| Vartul | 244 | KLTKITNLNV | 243 | 94 |
| Vartul | 15 | FMQLVELDV | 231 | 95 |
| Vartul | 1199 | KLDYrALAAV | 224 | 96 |
| Vartul | 68 | ALNDvSLQAL | 201 | 97 |
| Vartul | 63 | SLAHIALNDV | 160 | 98 |
| Vartul | 992 | ILAVNGQDV | 118 | 99 |
| Vartul | 849 | VLSINGVDV | 118 | 100 |
| Vartul | 129 | ALPNIRELWL | 117 | 101 |
| MGMT | 98 | VLWKLLKVV | 925 | 102 |
| MGMT | 161 | GLAVKEWLL | 160 | 103 |
| MGMT | 167 | WLLAhEGHRL | 364 | 104 |
| MGMT | 89 | FQQEsFTRQV | 101 | 105 |
| N-Myc | 421 | VILKkATEYV | 162 | 106 |
| N-Myc | 440 | LLLEkEKLQA | 128 | 107 |
| N-Myc | 446 | KLQArQQQLL | 75 | 108 |
| MAGI-2 | 65 | LLLEvNETPV | 1794 | 109 |
| MAGI-2 | 993 | KLIKdAGLSV | 243 | 110 |
| MAGI-2 | 970 | KVGDRILAV | 201 | 111 |
| MAGI-2 | 43 | YLGEvKPGKV | 171 | 112 |
| MAGI-2 | 76 | GLTIrDVLAV | 160 | 113 |
| MAGI-2 | 528 | AIMERPPPV | 145 | 114 |
| MAGI-2 | 751 | AIYESRQQV | 125 | 115 |
| MAGI-2 | 481 | VLGHTHADV | 118 | 116 |
| MAGI-2 | 639 | GLCEGDLIV | 117 | 117 |
| MAGI-2 | 65 | LLLEvNETPV | 1794 | 118 |
| MAGI-2 | 993 | KLIKdAGLSV | 243 | 119 |
| MAGI-2 | 970 | KVGDRILAV | 201 | 120 |
| MAGI-2 | 43 | YLGEvKPGKV | 171 | 121 |
| MAGI-2 | 76 | GLTIrDVLAV | 160 | 122 |
| MAGI-2 | 528 | AIMERPPPV | 145 | 123 |
| MAGI-2 | 751 | AIYESRQQV | 125 | 124 |
| MAGI-2 | 481 | VLGHTHADV | 118 | 125 |
| MAGI-2 | 639 | GLCEGDLIV | 117 | 126 |
| MAGI-3 | 70 | VLLEvNGTPV | 1794 | 127 |
| MAGI-3 | 502 | FQLVpVNQYV | 660 | 128 |
| MAGI-3 | 503 | QLVPVNQYV | 383 | 129 |
| MAGI-3 | 11 | WLSKvQECAV | 320 | 130 |
| MAGI-3 | 923 | KVGDHISAV | 201 | 131 |
| MAGI-3 | 726 | KLDPSEVYL | 164 | 132 |
| MAGI-3 | 654 | NLTHIQVVEV | 160 | 133 |
| MAGI-3 | 200 | FQPDPVDQV | 150 | 134 |
| MAGI-3 | 1067 | NMGLFILRL | 135 | 135 |
| MAGI-3 | 1121 | LLLLrPGTGL | 134 | 136 |
| MAGI-3 | 1122 | LLLRPGTGL | 134 | 137 |
| MAGI-3 | 499 | VQMFQLVPV | 102 | 138 |
| MAGI-3 | 70 | VLLEvNGTPV | 98 | 139 |
| MAGI-3 | 502 | FQLVpVNQYV | 91 | 140 |
| MAGI-3 | 503 | QLVPVNQYV | 85 | 141 |
| MAGI-3 | 11 | WLSKvQECAV | 79 | 142 |
| Tuberin | 464 | KVLDVLSFV | 4088 | 143 |
| Tuberin | 176 | FLLVLVNLV | 2723 | 144 |
| Tuberin | 1060 | WLVGnKLVTV | 736 | 145 |
| Tuberin | 291 | LLRGAVFFV | 659 | 146 |
| Tuberin | 1702 | IVSDrNLPFV | 537 | 147 |
| Tuberin | 80 | ALWKAVADL | 408 | 148 |

TABLE 4-continued

Host cell proteins and HLA-A*0201 binding peptides

| Protein | Starting Pos | Sequence | T0.5 | SEQ ID NO. |
|---|---|---|---|---|
| | 1208 | WLMSLENPL | 364 | 149 |
| | 688 | LLFRvLLQCL | 309 | 150 |
| | 117 | GVLRaLFFKV | 248 | 151 |
| | 1065 | KLVTVTTSV | 243 | 152 |
| | 464 | KVLDvLSFVL | 236 | 153 |
| | 155 | YLEEeLADFV | 226 | 154 |
| | 258 | KLMRNLLGT | 222 | 155 |
| | 1033 | YVFSNFTAV | 197 | 156 |
| | 235 | SLPLFIVTL | 187 | 157 |
| | 612 | LQAFdFLFLL | 187 | 158 |
| | 617 | FLFLIRADSL | 178 | 159 |
| | 506 | KLATqLLVDL | 172 | 160 |
| | 360 | ILLNIIERL | 151 | 161 |

TABLE 5

Summary of peptide binding

| Source protein | No. peptides binding |
|---|---|
| BAK | 6/7 |
| DLG | 7/10 |
| CMYC | 2/4 |
| E6AP | 9/10 |
| MUPP1 | 13/15 |
| Retinoblastoma | 6/16 |
| Total | 43/62 |

TABLE 6

Frequency of CD8+ T cells recognising Rb peptide in healthy volunteers.
Peripheral blood lymphocytes from HLA-A2+ healthy donors were enriched for CD8+ T cells, then cultured for 14 days with Rb7 peptide and antigen presenting cells (APC) or Melan-A (Mart1$_{26-35}$) peptide. Cells were harvested and tested with HLA-A2/Rb7 pentamer or HLA-A2/Melan-A pentamer. The numbers of CD8+ pentamer+ T lymphocytes were measured by flow cytometry, excluding dead and CD14+ cells.

| | Frequency of CD8+ pentamer+ cells | |
|---|---|---|
| Donor | Rb | Melan A |
| 1 | 1/2500 | 1/24 |
| 2 | 1/1000 | 1/4 |
| 3 | 1/1000 | 1/3 |
| 4 | 1/909 | 1/3 |
| 5 | 1/120 | 1/4 |
| 6 | 1/3333 | 1/208 |
| 7 | 1/2000 | 1/3 |
| 8 | 1/2500 | 1/3 |

REFERENCES

1. Mandelboim, O., E. Vadai, M. Fridkin, A. Katz-Hillel, M. Feldman, G. Berke, and L. Eisenbach. 1995. Regression of established murine carcinoma metastases following vaccination with tumour-associated antigen peptides. *Nature Medicine.* 1:1179.
2. Heslop, H. E., and C. M. Rooney. 1997. Adoptive cellular immunotherapy for EBV lymphoproliferative disease. *Immunological Reviews* 157:217.
3. Overwijk, W. W., D. S. Lee, D. R. Surman, K. R. Irvine, C. E. Touloukian, C. C. Chan, M. W. Carroll, B. Moss, S. A. Rosenberg, and N. P. Restifo. 1999. Vaccination with a recombinant vaccinia virus encoding a "self" antigen induces autoimmune vitiligo and tumor cell destruction in mice: requirement for CD4(+) T lymphocytes. *Proceedings of the National Academy of Sciences of the United States of America* 96:2982.
4. Gao, L., I. Bellantuono, A. Elsasser, S. B. Marley, M. Y. Gordon, J. M. Goldman, and H. J. Stauss. 2000. Selective elimination of leukemic CD34(+) progenitor cells by cytotoxic T lymphocytes specific for WT1. *Blood* 95:2198.
5. Theobald, M., J. Biggs, D. Dittmer, A. J. Levine, and L. A. Sherman. 1996. Targeting p53 as a general tumour antigen. *Proceedings of the National Academy of Sciences of the United States of America* 92:11993.
6. Walboomers, J. M., M. V. Jacobs, M. M. Manos, F. X. Bosch, J. A. Kummer, K. V. Shah, P. J. Snijders, J. Peto, C. J. Meijer, and N. Munoz. 1999. Human papillomavirus is a necessary cause of invasive cervical cancer worldwide. *Journal of Pathology* 189:12.
7. Borysiewicz, L. K., A. Fiander, M. Nimako, S. Man, G. W. G. Wilkinson, D. Westmoreland, A. S. Evans, M. Adams, S. N. Stacey, M. E. G. Boursnell, E. Rutherford, J. K. Hickling, and S. C. Inglis. 1996. A recombinant vaccinia virus encoding human papillomavirus type 16 and type 18, e6 and e7 proteins as immunotherapy for cervical cancer. *Lancet* 347:1523.
8. Nimako, M., A. N. Fiander, G. W. Wilkinson, L. K. Borysiewicz, and S. Man. 1997. Human papillomavirus-specific cytotoxic T lymphocytes in patients with cervical intraepithelial neoplasia grade III. *Cancer Res* 57:4855.
9. Evans, E. M., S. Man, A. S. Evans, and L. K. Borysiewicz. 1997. Infiltration of cervical cancer tissue with human papillomavirus-specific cytotoxic T-lymphocytes. *Cancer Res* 57:2943.
10. Youde, S. J., P. R. Dunbar, E. M. Evans, A. N. Fiander, L. K. Borysiewicz, V. Cerundolo, and S. Man. 2000. Use of fluorogenic histocompatibility leukocyte antigen-A*0201/HPV 16 E7 peptide complexes to isolate rare human cytotoxic T-lymphocyte-recognizing endogenous human papillomavirus antigens. *Cancer Res* 60:365.
11. Frazer, I. H., R. Thomas, J. Zhou, G. R. Leggatt, L. Dunn, N. McMillan, R. W. Tindle, L. Filgueira, P. Manders, P. Barnard, and M. Sharkey. 1999. Potential strategies utilised by papillomavirus to evade host immunity. *Immunological Reviews* 168:131.
12. Khammanivong, V., X. S. Liu, W. J. Liu, S. J. Rodda, G. R. Leggatt, R. W. Tindle, I. H. Frazer, and G. J. Fernando. 2003. Paucity of functional CTL epitopes in the E7 oncoprotein of cervical cancer associated human papillomavirus type 16. *Immunol Cell Biol* 81:1.
13. Scheffner, M., Munger K, Huibregtse J M, and H. P M. 1992. Targeted degradation of the retinoblastoma protein by human papillomavirus E7-E6 fusion proteins. *European Molecular Biology Organisation Journal* 11:2425.
14. Scheffner, M., B. A. Werness, J. M. Huigbretse, A. J. Levine, and P. M. Howley. 1990. The E6 oncoprotein encoded by human papillomavirus types 16 and 18 promotes the degradation of p53. *Cell* 63:1129.
15. Higashitsuji, H., K. Itoh, T. Nagao, S. Dawson, K. Nonoguchi, T. Kido, R. J. Mayer, S. Arii, and J. Fujita. 2000. Reduced stability of retinoblastoma protein by gankyrin, an oncogenic ankyrin-repeat protein overexpressed in hepatomas. *Nature Medicine* 6:96.
16. Rongcun, Y., F. Salazar-Onfray, J. Charo, K. Malmberg, K. Evrin, H. Maes, K. Kono, C. Hising, M. Petersson, O.

Larsson, L. Lan, E. Appella, A. Sette, E. Celis, and R. Kiessling. 1999. Identification of New HER2/neu-Derived Peptide Epitopes That Can Elicit Specific CTL Against Autologous and Allogeneic Carcinomas and Melanomas 1. *The Journal of Immunology:* 163:1037-1044.

17. Vonderheide, R. H., W. C. Hahn, J. L. Schultze, and L. M. Nadler. 1999. The telomerase catalytic subunit is a widely expressed tumor-associated antigen recognized by cytotoxic T lymphocytes. *Immunity* 10:673.

18. Berezutskaya, E., and S. Bagchi. 1997. The human papillomavirus E7 oncoprotein functionally interacts with the S4 subunit of the 26 S proteasome *J Biol Chem* 272:30135.

19. Boyer, S. N., D. E. Wazer, and V. Band. 1996. E7 protein of human papilloma virus 16 induces degradation of retinoblastoma protein through the ubiquitin proteasome pathway. *Cancer research* 56:4620.

20. Michalek, M. T., E. P. Grant, C. Gramm, A. L. Goldberg, and K. L. Rock. 1993. A role for the ubiquitin-dependent proteolytic pathway in MHC class I-restricted antigen presentation. *Nature* 363:552.

21. Cerundolo, V., A. Benham, V. Braud, S. Mukherjee, K. Gould, B. Macino, J. Neefjes, and A. Townsend. 1997. The proteasome-specific inhibitor lactacystin blocks presentation of cytotoxic T lymphocyte epitopes in human and murine cells. *Eur J Immunol* 27:336.

22. Vierboom, M., S. Zwaveling, G. Bos, M. Ooms, G. Krietemeijer, C. Melief, and R. Offringa. 2000. High Steady-State Levels of p53 Are Not a Prerequisite for Tumor Eradication by Wild-Type p53-specific Cytotoxic T Lymphocytes. *Cancer Research* 60:5508-5513.

23. Vierboom, M. P., H. W. Nijman, R. Offringa, E. I. van der Voort, T. van Hall, L. van den Broek, G. J. Fleuren, P. Kenemans, W. M. Kast, and C. J. Melief. 1997. Tumor eradication by wild-type p53-specific cytotoxic T lymphocytes. *Journal of Experimental Medicine* 186:695.

24. Kao, W. H., S. L. Beaudenon, A. L. Talis, J. M. Huibregtse, and P. M. Howley. 2000. Human Papillomavirus Type 16 E6 Induces Self-Ubiquitination of the E6AP Ubiquitin-Protein Ligase. *J. Virol.* 74:6408.

25. Gross-Mesilaty, S., E. Reinstein, B. Bercovich, K. E. Tobias, A. L. Schwartz, C. Kahana, and A. Ciechanover. 1998. Basal and human papillomavirus E6 oncoprotein-induced degradation of Myc proteins by the ubiquitin pathway. *Proceedings of the National Academy of Sciences of the United States of America* 95:8058.

26. Nakagawa, S., and J. M. Huibregtse. 2000. Human scribble (Vartul) is targeted for ubiquitin-mediated degradation by the high-risk papillomavirus E6 proteins and the E6AP ubiquitin-protein ligase. *Mol Cell Biol* 20:8244.

27. Kuhne, C., and L. Banks. 1998. E3-ubiquitin ligaselE6-AP links multicopy maintenance protein 7 to the ubiquitination pathway by a novel motif, the L2G box. *J Biol Chem* 273:34302.

28. Glaunsinger, B. A., S. S. Lee, M. Thomas, L. Banks, and R. Javier. 2000. Interactions of the PDZ-protein MAGI-1 with adenovirus E4-ORF1 and high-risk papillomavirus E6 oncoproteins. *Oncogene* 19:5270.

29. Gao, Q., L. Singh, A. Kumar, S. Srinivasan, D. E. Wazer, and V. Band. 2001. Human papillomavirus type 16 E6-induced degradation of E6TP1 correlates with its ability to immortalize human mammary epithelial cells. *J Virol* 75:4459.

30. Pim, D., M. Thomas, R. Javier, D. Gardiol, and L. Banks. 2000. HPV E6 targeted degradation of the discs large protein: evidence for the involvement of a novel ubiquitin ligase *Oncogene* 19:719.

31. Thomas, M., and L. Banks. 1998. Inhibition of Bak-induced apoptosis by HPV-18 E6. *Oncogene* 17:2943.

32. Lee, S., B. Glaunsinger, F. Mantovani, L. Banks, and R. Javier. 2000. Multi-PDZ Domain Protein MUPP1 Is a Cellular Target for both Adenovirus E4-ORF1 and High-Risk Papillomavirus Type 18 E6 Oncoproteins. *Journal of Virology* 74:9680-9693.

33. Srivenugopal, K. S., and F. Ali-Osman. 2002. The DNA repair protein, O(6)-Methylguanine-DNA methyltransferase is a proteolytic target for the E6 human papillomavirus oncoprotein. *Oncogene* 21:5940.

34. Thomas, M., R. Laura, K. Hepner, E. Guccione, C. Sawyers, L. Lasky, and L. Banks. 2002. Oncogenic human papillomavirus E6 proteins target the MAGI-2 and MAGI-3 proteins for degradation. *Oncogene* 21:5088.

35. Lu, Z., X. Hu, Y. Li, L. Zheng, Y. Zhou, H. Jiang, T. Ning, Z. Basang, C. Zhang, and Y. Ke. 2004. Human papillomavirus 16 E6 oncoprotein interferences with insulin signaling pathway by binding to tuberin. *J Biol Chem In press.*

36. Parker, K. C., M. A. Bednarek, L. K. Hull, U. Utz, B. Cunningham, H. J. Zweerink, W. E. Biddison, and J. E. Coligan. 1992. Sequence motifs important for peptide binding to the human MHC class I molecule, HLA-A2. *Journal of Immunology* 149:3580.

37. Engelhard, V. H.1994. Structure of peptides associated with MHC class I molecules. *Current Opinion in Immunology* 6:13.

38. Ellis, J. R., P. J. Keating, J. Baird, E. F. Hounsell, D. V. Renouf, M. Rowe, D. Hopkins, M. F. Duggan-Keen, J. S. Bartholomew, L. S. Young, and P. L. Stern. 1995. The association of an HPV16 oncogene variant with HLA-B7 has implications for vaccine design in cervical cancer. *Nature Medicine* 1:464.

39. Faulkner, L., L. K. Borysiewicz, and S. Man. 1998. The use of human leucocyte antigen class I transgenic mice to investigate human immune function. *J Immunol Methods* 221:1.

40. Dunbar, P., J. Chen, D. Chao, N. Rust, H. Teisserenc, G. Ogg, P. Romero, P. Weynants, and V. Cerundolo. 1999. Rapid cloning of tumour specific CTL suitable for adoptive immunotherapy of melanoma. *Journal of Immunology* 162:6959.

41. Rooney, C. M., C. A. Smith, C. Y. C. Ng, S. K. Loftin, J. W. Sixbey, Y. Gan, D. K. Srivastava, L. C. Bowman, R. A. Krance, M. K. Brenner, and H. E. Heslop. 1998. Infusion of cytotoxic T cells for the prevention and treatment of epstein-barr virus-induced lymphoma in allogeneic transplant recipients *Blood* 92:1549.

42. Stanislawski, T., R. H. Voss, C. Lotz, E. Sadovnikova, R. A. Willemsen, J. Kuball, T. Ruppert, R. L. Bolhuis, C. J. Melief, C. Huber, H. J. Stauss, and M. Theobaid. 2001. Circumventing tolerance to a human MDM2-derived tumor antigen by TCR gene transfer. *Nat Immunol* 2:962.

43. Shah, K. V. 1998. Do human papillomavirus infections cause oral cancer? *J Natl Cancer Inst* 90:1585.

44. Shamanin, V., H. zur Hausen, D. Layergne, C. M. Proby, I. M. Leigh, C. Neumann, H. Hamm, M. Goos, U.-F. Haustein, E. G. Jung, G. Plewig, H. Wolff, and E.-M. de Villiers. 1996. Human papillomavirus infections in nonmelanoma skin cancers from renal transplant recipients and nonimmunosuppressed patients. *Journal of the National Cancer Institute* 88:802.

45. Kiviat, N. B. 1999. Papillomaviruses in non-melanoma skin cancer: epidemiological aspects. *Semin Cancer Biol* 9:397.

46. Man, S., and A. Fiander. 2001. Immunology of human papillomavirus infection in lower genital tract neoplasia. *Best Pract Res Clin Obstet Gynaecol* 15:701.
47. Palefsky, J. M. 1997. Cutaneous and genital HPV-associated lesions in HIV-infected patients. *Clin Dermatol* 15:439.
48. De Luca, A., A. Baldi, V. Esposito, C. M. Howard, L. Bagella, P. Rizzo, M. Caputi, H. I. Pass, G. G. Giordano, F. Baldi, M. Carbone, and A. Giordano. 1997. The retinoblastoma gene family pRb/p105, p107, pRb2/p130 and simian virus-40 large T-antigen in human mesotheliomas *Nature Medicine* 3:913.
49. Li, B., and Q. P. Dou. 2000. Bax degradation by the ubiquitin/proteasome-dependent pathway: involvement in tumor survival and progression. *Proc Natl Acad Sci USA* 97:3850.
50. Pittet, M. J., Valmori, D., Dunbar, P. R., Speiser, D. E., Linard, D., Lejeune, F., Fleischhauer, K., Cerundolo, V., Cerottini, J. C., and Romero, P. 1999. High Frequencies of Naive Melan-A/MART-1-specific CD8(+) T Cells in a Large Proportion of Human. Histocompatibility Leukocyte Antigen (HLA)-A2 Individuals. *Journal of Experimental Medicine* 190:705-716.

The invention claimed is:

1. An immunogenic composition comprising: at least one isolated, purified, synthesised or recombinant peptide, wherein the peptide is selected from the group consisting of SEQ ID NO:2, SEQ ID NO:4, SEQ ID NO:6, SEQ ID NO:7, SEQ ID NO:8, SEQ ID NO:11, SEQ ID NO:12, SEQ ID NO:13, SEQ ID NO:14, and SEQ ID NO:16.

2. An immunogenic composition comprising: at least one isolated, purified, synthesised or recombinant peptide selected from the group consisting of SEQ ID NO:2, SEQ ID NO:4, SEQ ID NO:6, SEQ ID NO:7, SEQ ID NO:8, SEQ IDNO:11, SEQ ID NO:12, SEQ ID NO:13, SEQ ID NO:14, and SEQ ID NO:16 and, further at least one isolated, purified, synthesized or recombinant HLA molecule.

3. An isolated peptide selected from the group consisting of SEQ ID NO:2, SEQ ID NO:4, SEQ ID NO:6, SEQ ID NO:7, SEQ ID NO:8, SEQ ID NO:11, SEQ ID NO:12, SEQ ID NO:13, SEQ ID NO:14, and SEQ ID NO:16.

4. A complex comprising: at least one peptide selected from the group consisting of SEQ ID NO:2, SEQ ID NO:4, SEQ ID NO:6, SEQ ID NO:7, SEQ ID NO:8, SEQ ID NO:11, SEQ ID NO:12, SEQ ID NO:13, SEQ ID NO:14, and SEQ ID NO:16 in association with an HLA molecule.

5. A complex according to claim 4, wherein the HLA molecule is HLA-A molecule.

6. A complex according to any one of claims 4 or 5, wherein the HLA molecule is HLA-0201.

* * * * *

```
                        SEQUENCE LISTING

<160> NUMBER OF SEQ ID NOS: 161

<210> SEQ ID NO 1
<211> LENGTH: 10
<212> TYPE: PRT
<213> ORGANISM: Human

<400> SEQUENCE: 1

Trp Leu Ser Asp Ser Pro Leu Phe Asp Leu
1               5                   10

<210> SEQ ID NO 2
<211> LENGTH: 10
<212> TYPE: PRT
<213> ORGANISM: Human

<400> SEQUENCE: 2

Lys Leu Leu Asn Asp Asn Ile Phe His Met
1               5                   10

<210> SEQ ID NO 3
<211> LENGTH: 10
<212> TYPE: PRT
<213> ORGANISM: Human

<400> SEQUENCE: 3

Trp Leu Thr Trp Glu Lys Val Ser Ser Val
1               5                   10

<210> SEQ ID NO 4
<211> LENGTH: 9
<212> TYPE: PRT
<213> ORGANISM: Human

<400> SEQUENCE: 4

Ser Leu Ser Leu Phe Tyr Lys Lys Val
1               5

<210> SEQ ID NO 5
<211> LENGTH: 10
<212> TYPE: PRT
<213> ORGANISM: Human

<400> SEQUENCE: 5

Lys Leu Gly Val Arg Leu Tyr Tyr Arg Val
1               5                   10

<210> SEQ ID NO 6
<211> LENGTH: 10
<212> TYPE: PRT
```

```
<213> ORGANISM: Human

<400> SEQUENCE: 6

Leu Met Leu Cys Val Leu Asp Tyr Phe Ile
1               5                   10

<210> SEQ ID NO 7
<211> LENGTH: 9
<212> TYPE: PRT
<213> ORGANISM: Human

<400> SEQUENCE: 7

Ser Leu Leu Ala Cys Ala Leu Glu Val
1               5

<210> SEQ ID NO 8
<211> LENGTH: 9
<212> TYPE: PRT
<213> ORGANISM: Human

<400> SEQUENCE: 8

Val Leu Phe Ala Leu Phe Ser Lys Leu
1               5

<210> SEQ ID NO 9
<211> LENGTH: 10
<212> TYPE: PRT
<213> ORGANISM: Human

<400> SEQUENCE: 9

Ser Leu Phe Tyr Lys Lys Val Tyr Arg Leu
1               5                   10

<210> SEQ ID NO 10
<211> LENGTH: 10
<212> TYPE: PRT
<213> ORGANISM: Human

<400> SEQUENCE: 10

Lys Met Thr Pro Arg Ser Arg Ile Leu Val
1               5                   10

<210> SEQ ID NO 11
<211> LENGTH: 10
<212> TYPE: PRT
<213> ORGANISM: Human

<400> SEQUENCE: 11

Ile Ile Trp Thr Leu Phe Gln His Thr Leu
1               5                   10

<210> SEQ ID NO 12
<211> LENGTH: 9
<212> TYPE: PRT
<213> ORGANISM: Human

<400> SEQUENCE: 12

Ala Leu Val Leu Lys Val Ser Trp Ile
1               5

<210> SEQ ID NO 13
<211> LENGTH: 9
<212> TYPE: PRT
<213> ORGANISM: Human
```

```
<400> SEQUENCE: 13

Leu Thr Trp Glu Lys Val Ser Ser Val
1               5

<210> SEQ ID NO 14
<211> LENGTH: 9
<212> TYPE: PRT
<213> ORGANISM: Human

<400> SEQUENCE: 14

Ile Met Met Cys Ser Met Tyr Gly Ile
1               5

<210> SEQ ID NO 15
<211> LENGTH: 10
<212> TYPE: PRT
<213> ORGANISM: Human

<400> SEQUENCE: 15

Lys Leu Ala Glu Met Thr Ser Thr Arg Thr
1               5                   10

<210> SEQ ID NO 16
<211> LENGTH: 9
<212> TYPE: PRT
<213> ORGANISM: Human

<400> SEQUENCE: 16

Met Leu Cys Val Leu Asp Tyr Phe Ile
1               5

<210> SEQ ID NO 17
<211> LENGTH: 10
<212> TYPE: PRT
<213> ORGANISM: Human

<400> SEQUENCE: 17

Phe Leu Gly Gln Val Thr Arg Phe Val Val
1               5                   10

<210> SEQ ID NO 18
<211> LENGTH: 9
<212> TYPE: PRT
<213> ORGANISM: Human

<400> SEQUENCE: 18

Ala Leu Leu Gly Phe Gly Tyr Arg Leu
1               5

<210> SEQ ID NO 19
<211> LENGTH: 10
<212> TYPE: PRT
<213> ORGANISM: Human

<400> SEQUENCE: 19

Ile Leu Asn Val Leu Val Val Leu Gly Val
1               5                   10

<210> SEQ ID NO 20
<211> LENGTH: 10
<212> TYPE: PRT
<213> ORGANISM: Human

<400> SEQUENCE: 20
```

```
Asn Leu Gly Asn Gly Pro Ile Leu Asn Val
1               5                   10
```

<210> SEQ ID NO 21
<211> LENGTH: 9
<212> TYPE: PRT
<213> ORGANISM: Human

<400> SEQUENCE: 21

```
Val Val Leu Leu Gly Gln Phe Val Val
1               5
```

<210> SEQ ID NO 22
<211> LENGTH: 10
<212> TYPE: PRT
<213> ORGANISM: Human

<400> SEQUENCE: 22

```
Val Leu Val Val Leu Gly Val Val Leu Leu
1               5                   10
```

<210> SEQ ID NO 23
<211> LENGTH: 9
<212> TYPE: PRT
<213> ORGANISM: Human

<400> SEQUENCE: 23

```
Gly Leu Thr Gly Phe Leu Gly Gln Val
1               5
```

<210> SEQ ID NO 24
<211> LENGTH: 9
<212> TYPE: PRT
<213> ORGANISM: Human

<400> SEQUENCE: 24

```
Ala Leu Tyr Asp Arg Leu Ala Asp Val
1               5
```

<210> SEQ ID NO 25
<211> LENGTH: 10
<212> TYPE: PRT
<213> ORGANISM: Human

<400> SEQUENCE: 25

```
Asn Leu His Gly Val Phe Val Ala Glu Val
1               5                   10
```

<210> SEQ ID NO 26
<211> LENGTH: 9
<212> TYPE: PRT
<213> ORGANISM: Human

<400> SEQUENCE: 26

```
Gly Leu Pro Gly Asp Ser Phe Tyr Ile
1               5
```

<210> SEQ ID NO 27
<211> LENGTH: 10
<212> TYPE: PRT
<213> ORGANISM: Human

<400> SEQUENCE: 27

```
Gln Leu Leu Glu Phe Asn Gly Ile Asn Leu
1               5                   10
```

```
<210> SEQ ID NO 28
<211> LENGTH: 9
<212> TYPE: PRT
<213> ORGANISM: Human

<400> SEQUENCE: 28

Val Leu Trp Ile Pro Ala Cys Pro Leu
1               5

<210> SEQ ID NO 29
<211> LENGTH: 10
<212> TYPE: PRT
<213> ORGANISM: Human

<400> SEQUENCE: 29

Val Leu Ile Leu Gly Pro Leu Leu Asp Val
1               5                   10

<210> SEQ ID NO 30
<211> LENGTH: 10
<212> TYPE: PRT
<213> ORGANISM: Human

<400> SEQUENCE: 30

Leu Ile Leu Glu Tyr Gly Ser Leu Asp Val
1               5                   10

<210> SEQ ID NO 31
<211> LENGTH: 10
<212> TYPE: PRT
<213> ORGANISM: Human

<400> SEQUENCE: 31

Ser Leu Ala Tyr Gln Arg Val Gln Lys Val
1               5                   10

<210> SEQ ID NO 32
<211> LENGTH: 9
<212> TYPE: PRT
<213> ORGANISM: Human

<400> SEQUENCE: 32

Leu Ile Leu Gly Pro Leu Leu Asp Val
1               5

<210> SEQ ID NO 33
<211> LENGTH: 9
<212> TYPE: PRT
<213> ORGANISM: Human

<400> SEQUENCE: 33

Ile Leu Ala Gln Tyr Asn Pro His Val
1               5

<210> SEQ ID NO 34
<211> LENGTH: 10
<212> TYPE: PRT
<213> ORGANISM: Human

<400> SEQUENCE: 34

Tyr Leu Thr Glu Glu Lys Val Tyr Glu Ile
1               5                   10
```

```
<210> SEQ ID NO 35
<211> LENGTH: 9
<212> TYPE: PRT
<213> ORGANISM: Human

<400> SEQUENCE: 35

Phe Ile Asn Glu Pro Leu Asn Glu Val
1               5

<210> SEQ ID NO 36
<211> LENGTH: 10
<212> TYPE: PRT
<213> ORGANISM: Human

<400> SEQUENCE: 36

Tyr Leu Phe Arg Pro Glu Glu Ile Glu Leu
1               5                   10

<210> SEQ ID NO 37
<211> LENGTH: 9
<212> TYPE: PRT
<213> ORGANISM: Human

<400> SEQUENCE: 37

Val Leu Tyr Gln Ser Leu Lys Asp Leu
1               5

<210> SEQ ID NO 38
<211> LENGTH: 9
<212> TYPE: PRT
<213> ORGANISM: Human

<400> SEQUENCE: 38

Val Leu Ile Arg Glu Phe Trp Glu Ile
1               5

<210> SEQ ID NO 39
<211> LENGTH: 9
<212> TYPE: PRT
<213> ORGANISM: Human

<400> SEQUENCE: 39

Lys Leu Gly Pro Asp Asp Val Ser Val
1               5

<210> SEQ ID NO 40
<211> LENGTH: 9
<212> TYPE: PRT
<213> ORGANISM: Human

<400> SEQUENCE: 40

Tyr Leu Asn Leu Phe Ile Ile Gly Met
1               5

<210> SEQ ID NO 41
<211> LENGTH: 10
<212> TYPE: PRT
<213> ORGANISM: Human

<400> SEQUENCE: 41

Val Leu Ile Arg Glu Phe Trp Glu Ile Val
1               5                   10

<210> SEQ ID NO 42
<211> LENGTH: 10
```

```
<212> TYPE: PRT
<213> ORGANISM: Human

<400> SEQUENCE: 42

Phe Met Thr Cys Pro Phe Ile Leu Asn Ala
1               5                   10

<210> SEQ ID NO 43
<211> LENGTH: 10
<212> TYPE: PRT
<213> ORGANISM: Human

<400> SEQUENCE: 43

Tyr Leu Ser Pro Asn Val Glu Cys Asp Leu
1               5                   10

<210> SEQ ID NO 44
<211> LENGTH: 10
<212> TYPE: PRT
<213> ORGANISM: Human

<400> SEQUENCE: 44

Cys Met Trp Ser Gly Phe Ser Ala Ala Ala
1               5                   10

<210> SEQ ID NO 45
<211> LENGTH: 10
<212> TYPE: PRT
<213> ORGANISM: Human

<400> SEQUENCE: 45

Gly Leu Cys Ser Pro Ser Tyr Val Ala Val
1               5                   10

<210> SEQ ID NO 46
<211> LENGTH: 9
<212> TYPE: PRT
<213> ORGANISM: Human

<400> SEQUENCE: 46

Tyr Leu Gln Asp Leu Ser Ala Ala Ala
1               5

<210> SEQ ID NO 47
<211> LENGTH: 9
<212> TYPE: PRT
<213> ORGANISM: Human

<400> SEQUENCE: 47

Cys Met Trp Ser Gly Phe Ser Ala Ala
1               5

<210> SEQ ID NO 48
<211> LENGTH: 10
<212> TYPE: PRT
<213> ORGANISM: Human

<400> SEQUENCE: 48

Leu Leu Pro Gly Asp Arg Leu Met Phe Val
1               5                   10

<210> SEQ ID NO 49
<211> LENGTH: 10
<212> TYPE: PRT
<213> ORGANISM: Human
```

```
<400> SEQUENCE: 49

Ala Met Trp Glu Ala Gly Ile Gln His Ile
1               5                   10

<210> SEQ ID NO 50
<211> LENGTH: 9
<212> TYPE: PRT
<213> ORGANISM: Human

<400> SEQUENCE: 50

Leu Leu Gly Glu Asn His Gln Asp Val
1               5

<210> SEQ ID NO 51
<211> LENGTH: 9
<212> TYPE: PRT
<213> ORGANISM: Human

<400> SEQUENCE: 51

Tyr Leu Leu Glu Gln Ser Ser Leu Ala
1               5

<210> SEQ ID NO 52
<211> LENGTH: 10
<212> TYPE: PRT
<213> ORGANISM: Human

<400> SEQUENCE: 52

Leu Leu Gly Ala Ile Ile Ile His Glu Val
1               5                   10

<210> SEQ ID NO 53
<211> LENGTH: 10
<212> TYPE: PRT
<213> ORGANISM: Human

<400> SEQUENCE: 53

Gly Leu Ala Asp Lys Pro Leu Phe Arg Ala
1               5                   10

<210> SEQ ID NO 54
<211> LENGTH: 10
<212> TYPE: PRT
<213> ORGANISM: Human

<400> SEQUENCE: 54

Thr Leu Leu Gly Glu Asn His Gln Asp Val
1               5                   10

<210> SEQ ID NO 55
<211> LENGTH: 10
<212> TYPE: PRT
<213> ORGANISM: Human

<400> SEQUENCE: 55

Ser Leu Leu Lys Thr Ala Lys Met Thr Val
1               5                   10

<210> SEQ ID NO 56
<211> LENGTH: 9
<212> TYPE: PRT
<213> ORGANISM: Human

<400> SEQUENCE: 56
```

```
Ile Leu Met Val Asn Gly Glu Asp Val
1               5
```

<210> SEQ ID NO 57
<211> LENGTH: 9
<212> TYPE: PRT
<213> ORGANISM: Human

<400> SEQUENCE: 57

```
Lys Val Gly Asp Gln Ile Leu Ala Val
1               5
```

<210> SEQ ID NO 58
<211> LENGTH: 10
<212> TYPE: PRT
<213> ORGANISM: Human

<400> SEQUENCE: 58

```
Leu Met Gln Gly Asp Gln Ile Leu Met Val
1               5                   10
```

<210> SEQ ID NO 59
<211> LENGTH: 9
<212> TYPE: PRT
<213> ORGANISM: Human

<400> SEQUENCE: 59

```
Lys Leu Phe Ser Gly Asp Glu Leu Leu
1               5
```

<210> SEQ ID NO 60
<211> LENGTH: 9
<212> TYPE: PRT
<213> ORGANISM: Human

<400> SEQUENCE: 60

```
Thr Leu Gln Asn Glu Ser Phe Leu Leu
1               5
```

<210> SEQ ID NO 61
<211> LENGTH: 10
<212> TYPE: PRT
<213> ORGANISM: Human

<400> SEQUENCE: 61

```
Gly Met Ser Ser Glu Gln Val Ala Gln Val
1               5                   10
```

<210> SEQ ID NO 62
<211> LENGTH: 9
<212> TYPE: PRT
<213> ORGANISM: Human

<400> SEQUENCE: 62

```
Leu Met Phe Val Asn Asp Val Asn Leu
1               5
```

<210> SEQ ID NO 63
<211> LENGTH: 9
<212> TYPE: PRT
<213> ORGANISM: Human

<400> SEQUENCE: 63

```
Ser Met Gly Ala Ile Val Trp Ala Val
```

```
1               5

<210> SEQ ID NO 64
<211> LENGTH: 10
<212> TYPE: PRT
<213> ORGANISM: Human

<400> SEQUENCE: 64

Val Leu Ile Glu Gln Glu Thr Lys Ser Val
1               5                   10

<210> SEQ ID NO 65
<211> LENGTH: 9
<212> TYPE: PRT
<213> ORGANISM: Human

<400> SEQUENCE: 65

Gly Leu Gly Gln Leu Gly Phe His Val
1               5

<210> SEQ ID NO 66
<211> LENGTH: 10
<212> TYPE: PRT
<213> ORGANISM: Human

<400> SEQUENCE: 66

Leu Leu Gly Ile Ser Asn Glu Phe Ile Val
1               5                   10

<210> SEQ ID NO 67
<211> LENGTH: 10
<212> TYPE: PRT
<213> ORGANISM: Human

<400> SEQUENCE: 67

Gln Met Ile Asp Leu Leu Arg Thr Ser Val
1               5                   10

<210> SEQ ID NO 68
<211> LENGTH: 10
<212> TYPE: PRT
<213> ORGANISM: Human

<400> SEQUENCE: 68

Val Leu Phe Ser Ser Thr Tyr Pro Ser Leu
1               5                   10

<210> SEQ ID NO 69
<211> LENGTH: 9
<212> TYPE: PRT
<213> ORGANISM: Human

<400> SEQUENCE: 69

Phe Leu Leu Ala Lys Val Ile Asn Ala
1               5

<210> SEQ ID NO 70
<211> LENGTH: 10
<212> TYPE: PRT
<213> ORGANISM: Human

<400> SEQUENCE: 70

Ser Leu Gly Ser Ser Val Met Ala Pro Val
1               5                   10
```

```
<210> SEQ ID NO 71
<211> LENGTH: 9
<212> TYPE: PRT
<213> ORGANISM: Human

<400> SEQUENCE: 71

Phe Leu Gln Leu Leu Gly Glu Arg Val
1               5

<210> SEQ ID NO 72
<211> LENGTH: 9
<212> TYPE: PRT
<213> ORGANISM: Human

<400> SEQUENCE: 72

Ile Leu Phe Asp Leu Asn Glu Ala Ile
1               5

<210> SEQ ID NO 73
<211> LENGTH: 9
<212> TYPE: PRT
<213> ORGANISM: Human

<400> SEQUENCE: 73

Lys Leu Ile Asp Leu Glu Ser Pro Thr
1               5

<210> SEQ ID NO 74
<211> LENGTH: 10
<212> TYPE: PRT
<213> ORGANISM: Human

<400> SEQUENCE: 74

Leu Leu Leu Glu Val Gln Gly Val Arg Val
1               5                   10

<210> SEQ ID NO 75
<211> LENGTH: 10
<212> TYPE: PRT
<213> ORGANISM: Human

<400> SEQUENCE: 75

Thr Leu Gln Glu Thr Ala Leu Pro Pro Val
1               5                   10

<210> SEQ ID NO 76
<211> LENGTH: 9
<212> TYPE: PRT
<213> ORGANISM: Human

<400> SEQUENCE: 76

Lys Val Gly Asp Arg Ile Leu Ala Val
1               5

<210> SEQ ID NO 77
<211> LENGTH: 10
<212> TYPE: PRT
<213> ORGANISM: Human

<400> SEQUENCE: 77

Phe Leu Thr Val Lys Glu Phe Leu Asp Leu
1               5                   10

<210> SEQ ID NO 78
```

```
<211> LENGTH: 10
<212> TYPE: PRT
<213> ORGANISM: Human

<400> SEQUENCE: 78

Gly Leu Pro Arg Tyr Asp Val Leu Gly Val
1               5                   10

<210> SEQ ID NO 79
<211> LENGTH: 10
<212> TYPE: PRT
<213> ORGANISM: Human

<400> SEQUENCE: 79

Leu Leu Val Gln Arg Gly Gly Leu Pro Val
1               5                   10

<210> SEQ ID NO 80
<211> LENGTH: 9
<212> TYPE: PRT
<213> ORGANISM: Human

<400> SEQUENCE: 80

Val Leu Gly His Thr His Ala Gln Val
1               5

<210> SEQ ID NO 81
<211> LENGTH: 9
<212> TYPE: PRT
<213> ORGANISM: Human

<400> SEQUENCE: 81

Arg Leu Ala Gln His Ile Thr Tyr Val
1               5

<210> SEQ ID NO 82
<211> LENGTH: 10
<212> TYPE: PRT
<213> ORGANISM: Human

<400> SEQUENCE: 82

Leu Leu Ser Arg Phe Asp Leu Leu Trp Leu
1               5                   10

<210> SEQ ID NO 83
<211> LENGTH: 9
<212> TYPE: PRT
<213> ORGANISM: Human

<400> SEQUENCE: 83

Lys Met Gln Glu His Ser Asp Gln Val
1               5

<210> SEQ ID NO 84
<211> LENGTH: 10
<212> TYPE: PRT
<213> ORGANISM: Human

<400> SEQUENCE: 84

Val Leu Ala Asp Gln Gly Val Cys Cys Ile
1               5                   10

<210> SEQ ID NO 85
<211> LENGTH: 10
<212> TYPE: PRT
```

<213> ORGANISM: Human

<400> SEQUENCE: 85

Ala Leu Ala Arg Leu Arg Met Val Asp Val
1               5                   10

<210> SEQ ID NO 86
<211> LENGTH: 10
<212> TYPE: PRT
<213> ORGANISM: Human

<400> SEQUENCE: 86

Lys Leu Met Arg Arg Tyr Ile Ala Met Cys
1               5                   10

<210> SEQ ID NO 87
<211> LENGTH: 9
<212> TYPE: PRT
<213> ORGANISM: Human

<400> SEQUENCE: 87

Leu Leu Leu Leu Leu Val Gly Gly Val
1               5

<210> SEQ ID NO 88
<211> LENGTH: 10
<212> TYPE: PRT
<213> ORGANISM: Human

<400> SEQUENCE: 88

Ala Leu Asp Glu Tyr Glu Glu Leu Asn Val
1               5                   10

<210> SEQ ID NO 89
<211> LENGTH: 10
<212> TYPE: PRT
<213> ORGANISM: Human

<400> SEQUENCE: 89

Lys Met Ala Glu Ala Asp Arg Thr Ala Ile
1               5                   10

<210> SEQ ID NO 90
<211> LENGTH: 10
<212> TYPE: PRT
<213> ORGANISM: Human

<400> SEQUENCE: 90

Lys Leu Leu Glu Val Asn Gly Val Ala Leu
1               5                   10

<210> SEQ ID NO 91
<211> LENGTH: 10
<212> TYPE: PRT
<213> ORGANISM: Human

<400> SEQUENCE: 91

Ser Leu Pro Ala Ser Leu Ser Phe Leu Val
1               5                   10

<210> SEQ ID NO 92
<211> LENGTH: 9
<212> TYPE: PRT
<213> ORGANISM: Human

```
<400> SEQUENCE: 92

Tyr Leu Leu Pro Gln Gln Pro Pro Leu
1               5

<210> SEQ ID NO 93
<211> LENGTH: 10
<212> TYPE: PRT
<213> ORGANISM: Human

<400> SEQUENCE: 93

Ile Leu Thr Glu Asn Leu Leu Met Ala Leu
1               5                   10

<210> SEQ ID NO 94
<211> LENGTH: 10
<212> TYPE: PRT
<213> ORGANISM: Human

<400> SEQUENCE: 94

Lys Leu Thr Lys Leu Thr Asn Leu Asn Val
1               5                   10

<210> SEQ ID NO 95
<211> LENGTH: 9
<212> TYPE: PRT
<213> ORGANISM: Human

<400> SEQUENCE: 95

Phe Met Gln Leu Val Glu Leu Asp Val
1               5

<210> SEQ ID NO 96
<211> LENGTH: 10
<212> TYPE: PRT
<213> ORGANISM: Human

<400> SEQUENCE: 96

Lys Leu Asp Tyr Arg Ala Leu Ala Ala Val
1               5                   10

<210> SEQ ID NO 97
<211> LENGTH: 10
<212> TYPE: PRT
<213> ORGANISM: Human

<400> SEQUENCE: 97

Ala Leu Asn Asp Val Ser Leu Gln Ala Leu
1               5                   10

<210> SEQ ID NO 98
<211> LENGTH: 10
<212> TYPE: PRT
<213> ORGANISM: Human

<400> SEQUENCE: 98

Ser Leu Ala His Leu Ala Leu Asn Asp Val
1               5                   10

<210> SEQ ID NO 99
<211> LENGTH: 9
<212> TYPE: PRT
<213> ORGANISM: Human

<400> SEQUENCE: 99
```

-continued

Ile Leu Ala Val Asn Gly Gln Asp Val
1               5

<210> SEQ ID NO 100
<211> LENGTH: 9
<212> TYPE: PRT
<213> ORGANISM: Human

<400> SEQUENCE: 100

Val Leu Ser Ile Asn Gly Val Asp Val
1               5

<210> SEQ ID NO 101
<211> LENGTH: 10
<212> TYPE: PRT
<213> ORGANISM: Human

<400> SEQUENCE: 101

Ala Leu Pro Asn Leu Arg Glu Leu Trp Leu
1               5                   10

<210> SEQ ID NO 102
<211> LENGTH: 9
<212> TYPE: PRT
<213> ORGANISM: Human

<400> SEQUENCE: 102

Val Leu Trp Lys Leu Leu Lys Val Val
1               5

<210> SEQ ID NO 103
<211> LENGTH: 9
<212> TYPE: PRT
<213> ORGANISM: Human

<400> SEQUENCE: 103

Gly Leu Ala Val Lys Glu Trp Leu Leu
1               5

<210> SEQ ID NO 104
<211> LENGTH: 10
<212> TYPE: PRT
<213> ORGANISM: Human

<400> SEQUENCE: 104

Trp Leu Leu Ala His Glu Gly His Arg Leu
1               5                   10

<210> SEQ ID NO 105
<211> LENGTH: 10
<212> TYPE: PRT
<213> ORGANISM: Human

<400> SEQUENCE: 105

Phe Gln Gln Glu Ser Phe Thr Arg Gln Val
1               5                   10

<210> SEQ ID NO 106
<211> LENGTH: 10
<212> TYPE: PRT
<213> ORGANISM: Human

<400> SEQUENCE: 106

Val Ile Leu Lys Lys Ala Thr Glu Tyr Val
1               5                   10

```
<210> SEQ ID NO 107
<211> LENGTH: 10
<212> TYPE: PRT
<213> ORGANISM: Human

<400> SEQUENCE: 107

Leu Leu Leu Glu Lys Glu Lys Leu Gln Ala
1               5                   10

<210> SEQ ID NO 108
<211> LENGTH: 10
<212> TYPE: PRT
<213> ORGANISM: Human

<400> SEQUENCE: 108

Lys Leu Gln Ala Arg Gln Gln Leu Leu
1               5                   10

<210> SEQ ID NO 109
<211> LENGTH: 10
<212> TYPE: PRT
<213> ORGANISM: Human

<400> SEQUENCE: 109

Leu Leu Leu Glu Val Asn Glu Thr Pro Val
1               5                   10

<210> SEQ ID NO 110
<211> LENGTH: 10
<212> TYPE: PRT
<213> ORGANISM: Human

<400> SEQUENCE: 110

Lys Leu Ile Lys Asp Ala Gly Leu Ser Val
1               5                   10

<210> SEQ ID NO 111
<211> LENGTH: 9
<212> TYPE: PRT
<213> ORGANISM: Human

<400> SEQUENCE: 111

Lys Val Gly Asp Arg Ile Leu Ala Val
1               5

<210> SEQ ID NO 112
<211> LENGTH: 10
<212> TYPE: PRT
<213> ORGANISM: Human

<400> SEQUENCE: 112

Tyr Leu Gly Glu Val Lys Pro Gly Lys Val
1               5                   10

<210> SEQ ID NO 113
<211> LENGTH: 10
<212> TYPE: PRT
<213> ORGANISM: Human

<400> SEQUENCE: 113

Gly Leu Thr Ile Arg Asp Val Leu Ala Val
1               5                   10
```

```
<210> SEQ ID NO 114
<211> LENGTH: 9
<212> TYPE: PRT
<213> ORGANISM: Human

<400> SEQUENCE: 114

Ala Ile Met Glu Arg Pro Pro Pro Val
1               5

<210> SEQ ID NO 115
<211> LENGTH: 9
<212> TYPE: PRT
<213> ORGANISM: Human

<400> SEQUENCE: 115

Ala Ile Tyr Glu Ser Arg Gln Gln Val
1               5

<210> SEQ ID NO 116
<211> LENGTH: 9
<212> TYPE: PRT
<213> ORGANISM: Human

<400> SEQUENCE: 116

Val Leu Gly His Thr His Ala Asp Val
1               5

<210> SEQ ID NO 117
<211> LENGTH: 9
<212> TYPE: PRT
<213> ORGANISM: Human

<400> SEQUENCE: 117

Gly Leu Cys Glu Gly Asp Leu Ile Val
1               5

<210> SEQ ID NO 118
<211> LENGTH: 10
<212> TYPE: PRT
<213> ORGANISM: Human

<400> SEQUENCE: 118

Leu Leu Leu Glu Val Asn Glu Thr Pro Val
1               5                   10

<210> SEQ ID NO 119
<211> LENGTH: 10
<212> TYPE: PRT
<213> ORGANISM: Human

<400> SEQUENCE: 119

Lys Leu Ile Lys Asp Ala Gly Leu Ser Val
1               5                   10

<210> SEQ ID NO 120
<211> LENGTH: 9
<212> TYPE: PRT
<213> ORGANISM: Human

<400> SEQUENCE: 120

Lys Val Gly Asp Arg Ile Leu Ala Val
1               5

<210> SEQ ID NO 121
<211> LENGTH: 10
```

```
<212> TYPE: PRT
<213> ORGANISM: Human

<400> SEQUENCE: 121

Tyr Leu Gly Glu Val Lys Pro Gly Lys Val
1               5                   10

<210> SEQ ID NO 122
<211> LENGTH: 10
<212> TYPE: PRT
<213> ORGANISM: Human

<400> SEQUENCE: 122

Gly Leu Thr Ile Arg Asp Val Leu Ala Val
1               5                   10

<210> SEQ ID NO 123
<211> LENGTH: 9
<212> TYPE: PRT
<213> ORGANISM: Human

<400> SEQUENCE: 123

Ala Ile Met Glu Arg Pro Pro Pro Val
1               5

<210> SEQ ID NO 124
<211> LENGTH: 9
<212> TYPE: PRT
<213> ORGANISM: Human

<400> SEQUENCE: 124

Ala Ile Tyr Glu Ser Arg Gln Gln Val
1               5

<210> SEQ ID NO 125
<211> LENGTH: 9
<212> TYPE: PRT
<213> ORGANISM: Human

<400> SEQUENCE: 125

Val Leu Gly His Thr His Ala Asp Val
1               5

<210> SEQ ID NO 126
<211> LENGTH: 9
<212> TYPE: PRT
<213> ORGANISM: Human

<400> SEQUENCE: 126

Gly Leu Cys Glu Gly Asp Leu Ile Val
1               5

<210> SEQ ID NO 127
<211> LENGTH: 10
<212> TYPE: PRT
<213> ORGANISM: Human

<400> SEQUENCE: 127

Val Leu Leu Glu Val Asn Gly Thr Pro Val
1               5                   10

<210> SEQ ID NO 128
<211> LENGTH: 10
<212> TYPE: PRT
<213> ORGANISM: Human
```

```
<400> SEQUENCE: 128

Phe Gln Leu Val Pro Val Asn Gln Tyr Val
1               5                   10

<210> SEQ ID NO 129
<211> LENGTH: 9
<212> TYPE: PRT
<213> ORGANISM: Human

<400> SEQUENCE: 129

Gln Leu Val Pro Val Asn Gln Tyr Val
1               5

<210> SEQ ID NO 130
<211> LENGTH: 10
<212> TYPE: PRT
<213> ORGANISM: Human

<400> SEQUENCE: 130

Trp Leu Ser Lys Val Gln Glu Cys Ala Val
1               5                   10

<210> SEQ ID NO 131
<211> LENGTH: 9
<212> TYPE: PRT
<213> ORGANISM: Human

<400> SEQUENCE: 131

Lys Val Gly Asp His Ile Ser Ala Val
1               5

<210> SEQ ID NO 132
<211> LENGTH: 9
<212> TYPE: PRT
<213> ORGANISM: Human

<400> SEQUENCE: 132

Lys Leu Asp Pro Ser Glu Val Tyr Leu
1               5

<210> SEQ ID NO 133
<211> LENGTH: 10
<212> TYPE: PRT
<213> ORGANISM: Human

<400> SEQUENCE: 133

Asn Leu Thr His Leu Gln Val Val Glu Val
1               5                   10

<210> SEQ ID NO 134
<211> LENGTH: 9
<212> TYPE: PRT
<213> ORGANISM: Human

<400> SEQUENCE: 134

Phe Gln Pro Asp Pro Val Asp Gln Val
1               5

<210> SEQ ID NO 135
<211> LENGTH: 9
<212> TYPE: PRT
<213> ORGANISM: Human

<400> SEQUENCE: 135
```

```
Asn Met Gly Leu Phe Ile Leu Arg Leu
1               5
```

```
<210> SEQ ID NO 136
<211> LENGTH: 10
<212> TYPE: PRT
<213> ORGANISM: Human

<400> SEQUENCE: 136

Leu Leu Leu Leu Arg Pro Gly Thr Gly Leu
1               5                   10
```

```
<210> SEQ ID NO 137
<211> LENGTH: 9
<212> TYPE: PRT
<213> ORGANISM: Human

<400> SEQUENCE: 137

Leu Leu Leu Arg Pro Gly Thr Gly Leu
1               5
```

```
<210> SEQ ID NO 138
<211> LENGTH: 9
<212> TYPE: PRT
<213> ORGANISM: Human

<400> SEQUENCE: 138

Val Gln Met Phe Gln Leu Val Pro Val
1               5
```

```
<210> SEQ ID NO 139
<211> LENGTH: 10
<212> TYPE: PRT
<213> ORGANISM: Human

<400> SEQUENCE: 139

Val Leu Leu Glu Val Asn Gly Thr Pro Val
1               5                   10
```

```
<210> SEQ ID NO 140
<211> LENGTH: 10
<212> TYPE: PRT
<213> ORGANISM: Human

<400> SEQUENCE: 140

Phe Gln Leu Val Pro Val Asn Gln Tyr Val
1               5                   10
```

```
<210> SEQ ID NO 141
<211> LENGTH: 9
<212> TYPE: PRT
<213> ORGANISM: Human

<400> SEQUENCE: 141

Gln Leu Val Pro Val Asn Gln Tyr Val
1               5
```

```
<210> SEQ ID NO 142
<211> LENGTH: 10
<212> TYPE: PRT
<213> ORGANISM: Human

<400> SEQUENCE: 142

Trp Leu Ser Lys Val Gln Glu Cys Ala Val
```

```
1               5                   10
```

<210> SEQ ID NO 143
<211> LENGTH: 9
<212> TYPE: PRT
<213> ORGANISM: Human

<400> SEQUENCE: 143

```
Lys Val Leu Asp Val Leu Ser Phe Val
1               5
```

<210> SEQ ID NO 144
<211> LENGTH: 9
<212> TYPE: PRT
<213> ORGANISM: Human

<400> SEQUENCE: 144

```
Phe Leu Leu Val Leu Val Asn Leu Val
1               5
```

<210> SEQ ID NO 145
<211> LENGTH: 10
<212> TYPE: PRT
<213> ORGANISM: Human

<400> SEQUENCE: 145

```
Trp Leu Val Gly Asn Lys Leu Val Thr Val
1               5                   10
```

<210> SEQ ID NO 146
<211> LENGTH: 9
<212> TYPE: PRT
<213> ORGANISM: Human

<400> SEQUENCE: 146

```
Leu Leu Arg Gly Ala Val Phe Phe Val
1               5
```

<210> SEQ ID NO 147
<211> LENGTH: 10
<212> TYPE: PRT
<213> ORGANISM: Human

<400> SEQUENCE: 147

```
Ile Val Ser Asp Arg Asn Leu Pro Phe Val
1               5                   10
```

<210> SEQ ID NO 148
<211> LENGTH: 9
<212> TYPE: PRT
<213> ORGANISM: Human

<400> SEQUENCE: 148

```
Ala Leu Trp Lys Ala Val Ala Asp Leu
1               5
```

<210> SEQ ID NO 149
<211> LENGTH: 9
<212> TYPE: PRT
<213> ORGANISM: Human

<400> SEQUENCE: 149

```
Trp Leu Met Ser Leu Glu Asn Pro Leu
1               5
```

<210> SEQ ID NO 150
<211> LENGTH: 10
<212> TYPE: PRT
<213> ORGANISM: Human

<400> SEQUENCE: 150

Leu Leu Phe Arg Val Leu Leu Gln Cys Leu
1               5                   10

<210> SEQ ID NO 151
<211> LENGTH: 10
<212> TYPE: PRT
<213> ORGANISM: Human

<400> SEQUENCE: 151

Gly Val Leu Arg Ala Leu Phe Phe Lys Val
1               5                   10

<210> SEQ ID NO 152
<211> LENGTH: 9
<212> TYPE: PRT
<213> ORGANISM: Human

<400> SEQUENCE: 152

Lys Leu Val Thr Val Thr Thr Ser Val
1               5

<210> SEQ ID NO 153
<211> LENGTH: 10
<212> TYPE: PRT
<213> ORGANISM: Human

<400> SEQUENCE: 153

Lys Val Leu Asp Val Leu Ser Phe Val Leu
1               5                   10

<210> SEQ ID NO 154
<211> LENGTH: 10
<212> TYPE: PRT
<213> ORGANISM: Human

<400> SEQUENCE: 154

Tyr Leu Glu Glu Glu Leu Ala Asp Phe Val
1               5                   10

<210> SEQ ID NO 155
<211> LENGTH: 9
<212> TYPE: PRT
<213> ORGANISM: Human

<400> SEQUENCE: 155

Lys Leu Met Arg Asn Leu Leu Gly Thr
1               5

<210> SEQ ID NO 156
<211> LENGTH: 9
<212> TYPE: PRT
<213> ORGANISM: Human

<400> SEQUENCE: 156

Tyr Val Phe Ser Asn Phe Thr Ala Val
1               5

<210> SEQ ID NO 157

```
<211> LENGTH: 9
<212> TYPE: PRT
<213> ORGANISM: Human

<400> SEQUENCE: 157

Ser Leu Pro Leu Phe Ile Val Thr Leu
1               5

<210> SEQ ID NO 158
<211> LENGTH: 10
<212> TYPE: PRT
<213> ORGANISM: Human

<400> SEQUENCE: 158

Leu Gln Ala Phe Asp Phe Leu Phe Leu Leu
1               5                   10

<210> SEQ ID NO 159
<211> LENGTH: 10
<212> TYPE: PRT
<213> ORGANISM: Human

<400> SEQUENCE: 159

Phe Leu Phe Leu Leu Arg Ala Asp Ser Leu
1               5                   10

<210> SEQ ID NO 160
<211> LENGTH: 10
<212> TYPE: PRT
<213> ORGANISM: Human

<400> SEQUENCE: 160

Lys Leu Ala Thr Gln Leu Leu Val Asp Leu
1               5                   10

<210> SEQ ID NO 161
<211> LENGTH: 9
<212> TYPE: PRT
<213> ORGANISM: Human

<400> SEQUENCE: 161

Ile Leu Leu Asn Ile Ile Glu Arg Leu
1               5
```